US008299052B2

(12) United States Patent
Flanner et al.

(10) Patent No.: US 8,299,052 B2
(45) Date of Patent: Oct. 30, 2012

(54) PHARMACEUTICAL COMPOSITIONS AND METHODS FOR IMPROVED BACTERIAL ERADICATION

(75) Inventors: Henry H. Flanner, Montgomery Village, MD (US); Robert Guttendorf, Gaithersburg, MD (US); Donald Treacy, Woodbine, MD (US); Susan P. Clausen, Ijamsville, MD (US); Beth A. Burnside, Bethesda, MD (US)

(73) Assignee: Shionogi Inc., Florham Park, NJ (US)

( * ) Notice: Subject to any disclaimer, the term of this patent is extended or adjusted under 35 U.S.C. 154(b) by 210 days.

(21) Appl. No.: 11/800,574

(22) Filed: May 7, 2007

(65) Prior Publication Data

US 2008/0050430 A1 Feb. 28, 2008

Related U.S. Application Data

(60) Provisional application No. 60/798,109, filed on May 5, 2006.

(51) Int. Cl.
A61K 31/43 (2006.01)
A61K 31/00 (2006.01)
A61K 9/22 (2006.01)

(52) U.S. Cl. ... 514/197; 514/192; 514/199; 514/210.05; 424/468

(58) Field of Classification Search .................. 424/468; 514/192, 210.05
See application file for complete search history.

(56) References Cited

U.S. PATENT DOCUMENTS

| | | | |
|---|---|---|---|
| 3,108,046 A | 10/1963 | Harbit |
| 3,870,790 A | 3/1975 | Lowey et al. |
| 4,007,174 A | 2/1977 | Laundon |
| 4,008,246 A | 2/1977 | Ochiai et al. |
| 4,018,918 A | 4/1977 | Ayer et al. |
| 4,048,306 A | 9/1977 | Maier et al. |
| 4,131,672 A | 12/1978 | Huffman |
| 4,175,125 A | 11/1979 | Huffman |
| 4,226,849 A | 10/1980 | Schor |
| 4,236,211 A | 11/1980 | Arvesen |
| 4,250,166 A | 2/1981 | Maekawa et al. |
| 4,331,803 A | 5/1982 | Watanabe et al. |
| 4,362,731 A | 12/1982 | Hill |
| 4,369,172 A | 1/1983 | Schor et al. |
| 4,399,151 A | 8/1983 | Sjoerdsma et al. |
| 4,430,495 A | 2/1984 | Patt et al. |
| 4,435,173 A | 3/1984 | Siposs et al. |
| 4,474,768 A | 10/1984 | Bright |
| 4,517,359 A | 5/1985 | Kobrehel et al. |
| 4,525,352 A | 6/1985 | Cole et al. |
| 4,529,720 A | 7/1985 | Cole et al. |
| 4,560,552 A | 12/1985 | Cole et al. |
| 4,568,741 A | 2/1986 | Livingston |
| 4,598,045 A | 7/1986 | Masover et al. |
| 4,616,008 A | 10/1986 | Hirai et al. |
| 4,634,697 A | 1/1987 | Hamashima |
| 4,644,031 A | 2/1987 | Lehmann et al. |
| 4,670,549 A | 6/1987 | Morimoto et al. |
| 4,672,109 A | 6/1987 | Watanabe et al. |
| 4,680,386 A | 7/1987 | Morimoto et al. |
| 4,710,565 A | 12/1987 | Livingston et al. |
| 4,723,958 A | 2/1988 | Pope et al. |
| 4,728,512 A | 3/1988 | Mehta et al. |
| 4,749,568 A | 6/1988 | Reusser et al. |
| 4,755,385 A | 7/1988 | Etienne et al. |
| 4,775,751 A | 10/1988 | McShane |
| 4,794,001 A | 12/1988 | Mehta et al. |
| 4,808,411 A | 2/1989 | Lu et al. |
| 4,812,561 A | 3/1989 | Hamashima et al. |
| 4,828,836 A | 5/1989 | Elger et al. |
| 4,831,025 A | 5/1989 | Godtfredsen et al. |
| 4,835,140 A | 5/1989 | Smith et al. |
| 4,842,866 A | 6/1989 | Horder et al. |
| 4,849,515 A | 7/1989 | Matier et al. |
| 4,879,135 A | 11/1989 | Greco et al. |
| 4,894,119 A | 1/1990 | Baron, Jr. et al. |
| 4,895,934 A | 1/1990 | Matier et al. |
| 4,904,476 A | 2/1990 | Mehta et al. |
| 4,915,953 A | 4/1990 | Jordan et al. |
| 4,945,080 A | 7/1990 | Lindstrom et al. |
| 4,945,405 A | 7/1990 | Hirota |
| 4,971,805 A | 11/1990 | Kitanishi et al. |
| 4,990,602 A | 2/1991 | Morimoto et al. |
| 5,011,692 A | 4/1991 | Fujioka et al. |

(Continued)

FOREIGN PATENT DOCUMENTS

EP 0052075 11/1981

(Continued)

OTHER PUBLICATIONS

Shvartzman et al., "Treatment of stretococcal pharyngitis with amoxycillin once a day," British Medical Journal, 1993; vol. 306: pp. 1170-1172.*

Aqoat AS-HF. http://www.signetchem.com/Signet-The-Complete-Excipients-Company-Product-SHIN-ETSU-AQOAT-HPMCAS, Published Dec. 8, 2009, Accessed Aug. 9, 2011.

Chhipa et al, "Formulation Optimization of Sustained Release Pellets of Itopride Hydrochloride using Different Polymers," Journal of Pharmacy Research 2009 2(8) 1404-1408.

Hilton et al. ("Use of Hydroxpropyl Methylcellulose Acetate Succinate in an Enteric Polymer Matrix to Design Controlled-Release Tablets of Amoxicillin Trihydrate," Journal of Pharmaceutical Sciences, vol. 82, No. 7, Jul. 1993, pp. 737-743).

(Continued)

*Primary Examiner* — Yong Chong
*Assistant Examiner* — Jody Karol
(74) *Attorney, Agent, or Firm* — MH2 Technology Law Group LLP

(57) ABSTRACT

A process for treating a bacterial infection with an antibiotic, comprising: administering to a patient with a bacterial infection a product that includes a modified release dosage form containing an antibiotic, said product being administered once-a-day in a dosage and for a number of days that provides a Total T>MIC sufficient to achieve at least the minimum amount of bacterial eradication for treatment of said bacterial infection.

10 Claims, 5 Drawing Sheets

U.S. PATENT DOCUMENTS

| | | | |
|---|---|---|---|
| 5,045,533 A | 9/1991 | Philippe et al. |
| 5,051,262 A | 9/1991 | Panoz et al. |
| 5,110,597 A | 5/1992 | Wong et al. |
| 5,110,598 A | 5/1992 | Kwan et al. |
| 5,143,661 A | 9/1992 | Lawter et al. |
| 5,158,777 A | 10/1992 | Abramowitz et al. |
| 5,178,874 A | 1/1993 | Kwan et al. |
| 5,182,374 A | 1/1993 | Tobkes et al. |
| 5,204,055 A | 4/1993 | Sachs et al. |
| 5,213,808 A | 5/1993 | Bar-Shalom et al. |
| 5,229,131 A | 7/1993 | Amidon et al. |
| 5,230,703 A | 7/1993 | Alon |
| 5,274,085 A | 12/1993 | Amano et al. |
| 5,288,503 A | 2/1994 | Wood et al. |
| 5,334,590 A | 8/1994 | DiNinno et al. |
| 5,340,656 A | 8/1994 | Sachs et al. |
| 5,358,713 A | 10/1994 | Shimamura |
| 5,387,380 A | 2/1995 | Cima et al. |
| 5,393,765 A | 2/1995 | Infeld et al. |
| 5,395,626 A | 3/1995 | Kotwal et al. |
| 5,395,628 A | 3/1995 | Noda et al. |
| 5,399,723 A | 3/1995 | Iinuma et al. |
| 5,401,512 A | 3/1995 | Rhodes et al. |
| 5,413,777 A | 5/1995 | Sheth et al. |
| 5,414,014 A | 5/1995 | Schneider et al. |
| 5,422,343 A | 6/1995 | Yamamoto et al. |
| 5,430,021 A | 7/1995 | Rudnic et al. |
| 5,445,829 A | 8/1995 | Paradissis et al. |
| 5,457,187 A | 10/1995 | Gmeiner et al. |
| 5,462,747 A | 10/1995 | Radebaugh et al. |
| 5,466,446 A | 11/1995 | Stiefel et al. |
| 5,472,708 A | 12/1995 | Chen |
| 5,476,854 A | 12/1995 | Young |
| 5,490,962 A | 2/1996 | Cima et al. |
| 5,508,040 A | 4/1996 | Chen |
| 5,518,680 A | 5/1996 | Cima et al. |
| 5,538,954 A | 7/1996 | Koch et al. |
| 5,543,417 A | 8/1996 | Waldstreicher |
| 5,556,839 A | 9/1996 | Greene et al. |
| 5,567,441 A | 10/1996 | Chen |
| 5,576,022 A | 11/1996 | Yang et al. |
| 5,578,713 A | 11/1996 | McGill, III |
| 5,599,557 A | 2/1997 | Johnson et al. |
| 5,607,685 A | 3/1997 | Cimbollek et al. |
| 5,633,006 A | 5/1997 | Catania et al. |
| 5,672,359 A | 9/1997 | Digenis et al. |
| 5,688,516 A | 11/1997 | Raad et al. |
| 5,702,895 A | 12/1997 | Matsunaga et al. |
| 5,705,190 A | 1/1998 | Broad et al. |
| 5,707,646 A | 1/1998 | Yajima et al. |
| 5,719,132 A | 2/1998 | Lin et al. |
| 5,719,272 A | 2/1998 | Yang et al. |
| 5,725,553 A | 3/1998 | Moenning |
| 5,733,886 A | 3/1998 | Baroody et al. |
| 5,756,473 A | 5/1998 | Liu et al. |
| 5,780,446 A | 7/1998 | Ramu |
| 5,789,584 A | 8/1998 | Christensen et al. |
| 5,808,017 A | 9/1998 | Chang |
| 5,817,321 A | 10/1998 | Alakhov et al. |
| 5,827,531 A | 10/1998 | Morrison et al. |
| 5,837,284 A | 11/1998 | Mehta et al. |
| 5,837,829 A | 11/1998 | Ku |
| 5,840,329 A | 11/1998 | Bai |
| 5,840,760 A | 11/1998 | Carraher, Jr. et al. |
| 5,844,105 A | 12/1998 | Liu et al. |
| 5,849,776 A | 12/1998 | Czemielewski et al. |
| 5,852,180 A | 12/1998 | Patel |
| 5,858,986 A | 1/1999 | Liu et al. |
| 5,864,023 A | 1/1999 | Ku et al. |
| 5,869,170 A | 2/1999 | Cima et al. |
| 5,872,104 A | 2/1999 | Vermeulen et al. |
| 5,872,229 A | 2/1999 | Liu et al. |
| 5,877,243 A | 3/1999 | Sarangapani |
| 5,883,079 A | 3/1999 | Zopf et al. |
| 5,892,008 A | 4/1999 | Ku et al. |
| 5,910,322 A | 6/1999 | Rivett et al. |
| 5,919,219 A | 7/1999 | Knowlton |
| 5,919,489 A | 7/1999 | Saleki-Gerhardt et al. |
| 5,919,916 A | 7/1999 | Gracey et al. |
| 5,929,219 A | 7/1999 | Hill |
| 5,932,710 A | 8/1999 | Liu et al. |
| 5,945,124 A | 8/1999 | Sachs et al. |
| 5,945,405 A | 8/1999 | Spanton et al. |
| 5,962,024 A | 10/1999 | Marvola et al. |
| 5,972,373 A | 10/1999 | Yajima et al. |
| 5,980,942 A | 11/1999 | Katzhendler et al. |
| 5,985,643 A | 11/1999 | Tomasz et al. |
| 5,998,194 A | 12/1999 | Summers, Jr. et al. |
| 6,008,195 A | 12/1999 | Selsted |
| 6,010,718 A | 1/2000 | Al-Razzak et al. |
| 6,013,507 A | 1/2000 | Tomasz et al. |
| 6,027,748 A | 2/2000 | Conte et al. |
| 6,031,093 A | 2/2000 | Cole et al. |
| 6,048,977 A | 4/2000 | Cole et al. |
| 6,051,255 A | 4/2000 | Conley et al. |
| 6,051,703 A | 4/2000 | Cole et al. |
| 6,057,291 A | 5/2000 | Hancock et al. |
| 6,059,816 A | 5/2000 | Moenning |
| 6,063,613 A | 5/2000 | De Lecanstre et al. |
| 6,063,917 A | 5/2000 | Ascher et al. |
| 6,068,859 A | 5/2000 | Curatolo et al. |
| 6,110,925 A | 8/2000 | Williams et al. |
| 6,117,843 A | 9/2000 | Baroody et al. |
| 6,120,803 A | 9/2000 | Wong et al. |
| 6,127,349 A | 10/2000 | Chasalow |
| 6,132,768 A | 10/2000 | Sachs et al. |
| 6,132,771 A | 10/2000 | Depui et al. |
| 6,136,587 A | 10/2000 | Tomasz et al. |
| 6,156,507 A | 12/2000 | Hiramatsu et al. |
| 6,159,491 A | 12/2000 | Durrani |
| 6,162,925 A | 12/2000 | Williams et al. |
| 6,183,778 B1 | 2/2001 | Conte et al. |
| 6,187,768 B1 | 2/2001 | Welle et al. |
| 6,214,359 B1 | 4/2001 | Bax |
| 6,218,380 B1 | 4/2001 | Cole et al. |
| 6,228,398 B1 | 5/2001 | Devane et al. |
| 6,231,875 B1 | 5/2001 | Sun et al. |
| 6,248,363 B1 | 6/2001 | Patel et al. |
| 6,251,647 B1 | 6/2001 | De Lencastre et al. |
| 6,265,394 B1 | 7/2001 | Sterzycki et al. |
| 6,270,805 B1 | 8/2001 | Chen et al. |
| 6,280,771 B1 | 8/2001 | Monkhouse et al. |
| 6,294,199 B1 | 9/2001 | Conley et al. |
| 6,294,526 B1 | 9/2001 | Higuchi et al. |
| 6,296,873 B1 | 10/2001 | Katzhendler et al. |
| 6,297,215 B1 | 10/2001 | Hancock et al. |
| 6,299,903 B1 | 10/2001 | Rivett et al. |
| 6,306,436 B1 | 10/2001 | Chungi et al. |
| 6,309,663 B1 | 10/2001 | Patel et al. |
| 6,322,819 B1 | 11/2001 | Burnside et al. |
| 6,333,050 B2 | 12/2001 | Wong et al. |
| 6,340,475 B2 | 1/2002 | Shell et al. |
| 6,352,720 B1 | 3/2002 | Martin et al. |
| 6,358,525 B1 | 3/2002 | Guo et al. |
| 6,358,528 B1 | 3/2002 | Grimmett et al. |
| 6,383,471 B1 | 5/2002 | Chen et al. |
| 6,384,081 B2 | 5/2002 | Berman |
| 6,391,614 B1 | 5/2002 | Tomasz et al. |
| 6,399,086 B1 | 6/2002 | Katzhendler et al. |
| 6,403,569 B1 | 6/2002 | Achterrath |
| 6,406,717 B2 | 6/2002 | Cherukuri |
| 6,406,880 B1 | 6/2002 | Thomton |
| 6,440,462 B1 | 8/2002 | Raneburger et al. |
| 6,444,796 B1 | 9/2002 | Suh et al. |
| 6,468,964 B1 | 10/2002 | Rowe |
| 6,479,496 B1 | 11/2002 | Wolff |
| 6,495,157 B1 | 12/2002 | Pena et al. |
| 6,497,901 B1 | 12/2002 | Royer |
| 6,503,709 B1 | 1/2003 | Bekkaoui et al. |
| 6,506,886 B1 | 1/2003 | Lee et al. |
| 6,514,518 B2 | 2/2003 | Monkhouse et al. |
| 6,515,010 B1 | 2/2003 | Franchini et al. |
| 6,515,116 B2 | 2/2003 | Suh et al. |
| 6,530,958 B1 | 3/2003 | Cima et al. |
| 6,541,014 B2 | 4/2003 | Rudnic et al. |
| 6,544,555 B2 | 4/2003 | Rudnic et al. |
| 6,548,084 B2 | 4/2003 | Leonard et al. |

| Patent/Pub No. | Date | Inventor |
|---|---|---|
| 6,550,955 B2 | 4/2003 | D'Silva |
| 6,551,584 B2 | 4/2003 | Bandyopadhyay et al. |
| 6,551,616 B1 | 4/2003 | Notario et al. |
| 6,558,699 B2 | 5/2003 | Venkatesh |
| 6,565,873 B1 | 5/2003 | Shefer et al. |
| 6,565,882 B2 | 5/2003 | Rudnic |
| 6,569,463 B2 | 5/2003 | Patel et al. |
| 6,585,997 B2 | 7/2003 | Moro et al. |
| 6,599,884 B2 | 7/2003 | Avrutov et al. |
| 6,605,069 B1 | 8/2003 | Albers et al. |
| 6,605,300 B1 | 8/2003 | Burnside et al. |
| 6,605,609 B2 | 8/2003 | Barbachyn et al. |
| 6,605,751 B1 | 8/2003 | Gibbins et al. |
| 6,610,323 B1 | 8/2003 | Lundberg et al. |
| 6,610,328 B2 | 8/2003 | Rudnic et al. |
| 6,617,436 B2 | 9/2003 | Avrutov et al. |
| 6,623,757 B2 | 9/2003 | Rudnic et al. |
| 6,623,758 B2 | 9/2003 | Rudnic et al. |
| 6,624,292 B2 | 9/2003 | Lifshitz et al. |
| 6,627,222 B2 | 9/2003 | Rudnic et al. |
| 6,627,223 B2 | 9/2003 | Percel et al. |
| 6,627,743 B1 | 9/2003 | Liu et al. |
| 6,630,498 B2 | 10/2003 | Gudipati et al. |
| 6,632,453 B2 | 10/2003 | Rudnic et al. |
| 6,635,280 B2 | 10/2003 | Shell et al. |
| 6,638,532 B2 | 10/2003 | Rudnic et al. |
| 6,642,276 B2 | 11/2003 | Wadhwa |
| 6,663,890 B2 | 12/2003 | Rudnic et al. |
| 6,663,891 B2 | 12/2003 | Rudnic et al. |
| 6,667,042 B2 | 12/2003 | Rudnic et al. |
| 6,667,057 B2 | 12/2003 | Rudnic et al. |
| 6,669,948 B2 * | 12/2003 | Rudnic et al. ................ 424/400 |
| 6,669,955 B2 | 12/2003 | Chungi et al. |
| 6,673,369 B2 | 1/2004 | Rampal et al. |
| 6,682,759 B2 | 1/2004 | Lim et al. |
| 6,696,426 B2 | 2/2004 | Singh et al. |
| 6,702,803 B2 | 3/2004 | Kupperblatt et al. |
| 6,706,273 B1 | 3/2004 | Roessler |
| 6,723,340 B2 | 4/2004 | Gusler et al. |
| 6,723,341 B2 | 4/2004 | Rudnic et al. |
| 6,730,320 B2 | 5/2004 | Rudnic et al. |
| 6,730,325 B2 | 5/2004 | Devane et al. |
| 6,735,470 B2 | 5/2004 | Henley et al. |
| 6,740,664 B2 | 5/2004 | Cagle et al. |
| 6,746,692 B2 | 6/2004 | Conley et al. |
| 6,756,057 B2 | 6/2004 | Storm et al. |
| 6,767,899 B1 | 7/2004 | Kay et al. |
| 6,777,420 B2 | 8/2004 | Zhi et al. |
| 6,783,773 B1 | 8/2004 | Storm et al. |
| 6,818,407 B2 | 11/2004 | Hancock et al. |
| 6,824,792 B2 | 11/2004 | Foreman et al. |
| 6,872,407 B2 | 3/2005 | Notario et al. |
| 6,878,387 B1 | 4/2005 | Petereit et al. |
| 6,906,035 B2 | 6/2005 | Hancock et al. |
| 6,929,804 B2 | 8/2005 | Rudnic et al. |
| 6,946,458 B2 | 9/2005 | Turos |
| 6,984,401 B2 | 1/2006 | Rudnic et al. |
| 6,991,807 B2 | 1/2006 | Rudnic et al. |
| 7,008,633 B2 | 3/2006 | Yang et al. |
| 2001/0046984 A1 | 11/2001 | Rudnic |
| 2001/0048944 A1 | 12/2001 | Rudnic et al. |
| 2002/0004070 A1 | 1/2002 | Rudnic et al. |
| 2002/0004499 A1 | 1/2002 | Rudnic et al. |
| 2002/0015728 A1 | 2/2002 | Payumo et al. |
| 2002/0028920 A1 | 3/2002 | Lifshitz et al. |
| 2002/0042394 A1 | 4/2002 | Hogenkamp et al. |
| 2002/0068078 A1 | 6/2002 | Rudnic et al. |
| 2002/0068085 A1 | 6/2002 | Rudnic et al. |
| 2002/0081332 A1 | 6/2002 | Rampal et al. |
| 2002/0103261 A1 | 8/2002 | Ninkov |
| 2002/0106412 A1 | 8/2002 | Rowe et al. |
| 2002/0115624 A1 | 8/2002 | Behar et al. |
| 2002/0119168 A1 | 8/2002 | Rudnic et al. |
| 2002/0136764 A1 | 9/2002 | Rudnic et al. |
| 2002/0136765 A1 | 9/2002 | Rudnic et al. |
| 2002/0136766 A1 | 9/2002 | Rudnic et al. |
| 2002/0150619 A1 | 10/2002 | Rudnic et al. |
| 2002/0197314 A1 | 12/2002 | Rudnic et al. |
| 2003/0012814 A1 | 1/2003 | Rudnic et al. |
| 2003/0018295 A1 | 1/2003 | Henley et al. |
| 2003/0049311 A1 | 3/2003 | McAllister et al. |
| 2003/0064100 A1 | 4/2003 | Rudnic et al. |
| 2003/0073647 A1 | 4/2003 | Chao et al. |
| 2003/0073648 A1 | 4/2003 | Chao et al. |
| 2003/0073826 A1 | 4/2003 | Chao et al. |
| 2003/0077323 A1 | 4/2003 | Rudnic et al. |
| 2003/0086969 A1 | 5/2003 | Rudnic et al. |
| 2003/0091627 A1 | 5/2003 | Sharma |
| 2003/0096006 A1 | 5/2003 | Rudnic et al. |
| 2003/0096007 A1 | 5/2003 | Rudnic et al. |
| 2003/0096008 A1 | 5/2003 | Rudnic et al. |
| 2003/0099706 A1 | 5/2003 | Rudnic et al. |
| 2003/0099707 A1 | 5/2003 | Rudnic et al. |
| 2003/0104054 A1 | 6/2003 | Rudnic et al. |
| 2003/0104055 A1 | 6/2003 | Rudnic et al. |
| 2003/0104056 A1 | 6/2003 | Rudnic et al. |
| 2003/0104058 A1 | 6/2003 | Rudnic et al. |
| 2003/0124196 A1 | 7/2003 | Weinbach et al. |
| 2003/0129236 A1 | 7/2003 | Heimlich et al. |
| 2003/0143268 A1 | 7/2003 | Pryce Lewis et al. |
| 2003/0147953 A1 | 8/2003 | Rudnic et al. |
| 2003/0190360 A1 | 10/2003 | Baichwal et al. |
| 2003/0198677 A1 | 10/2003 | Pryce Lewis et al. |
| 2003/0199808 A1 | 10/2003 | Henley et al. |
| 2003/0203023 A1 | 10/2003 | Rudnic et al. |
| 2003/0206951 A1 | 11/2003 | Rudnic et al. |
| 2003/0216555 A1 | 11/2003 | Lifshitz et al. |
| 2003/0216556 A1 | 11/2003 | Avrutov et al. |
| 2003/0232089 A1 | 12/2003 | Singh et al. |
| 2003/0235615 A1 | 12/2003 | Rudnic |
| 2004/0018234 A1 | 1/2004 | Rudnic et al. |
| 2004/0033262 A1 | 2/2004 | Kshirsagar et al. |
| 2004/0043073 A1 | 3/2004 | Chen et al. |
| 2004/0047906 A1 | 3/2004 | Percel et al. |
| 2004/0048814 A1 | 3/2004 | Vanderbist et al. |
| 2004/0052842 A1 | 3/2004 | Rudnic et al. |
| 2004/0058879 A1 | 3/2004 | Avrutov et al. |
| 2004/0091528 A1 | 5/2004 | Rogers et al. |
| 2004/0126427 A1 | 7/2004 | Venkatesh et al. |
| 2004/0126429 A1 | 7/2004 | Storm et al. |
| 2004/0176737 A1 | 9/2004 | Henley et al. |
| 2004/0208936 A1 | 10/2004 | Chorin et al. |
| 2004/0219223 A1 | 11/2004 | Kunz |
| 2004/0253249 A1 | 12/2004 | Rudnic et al. |
| 2004/0265379 A1 | 12/2004 | Conley et al. |
| 2005/0019403 A1 | 1/2005 | Burnside et al. |
| 2005/0053658 A1 | 3/2005 | Venkatesh et al. |
| 2005/0064033 A1 | 3/2005 | Notario et al. |
| 2005/0064034 A1 | 3/2005 | Li et al. |
| 2005/0142187 A1 | 6/2005 | Treacy et al. |
| 2005/0163857 A1 | 7/2005 | Rampal et al. |
| 2005/0203076 A1 | 9/2005 | Li et al. |
| 2005/0203085 A1 | 9/2005 | Li et al. |
| 2005/0209210 A1 | 9/2005 | Ding et al. |
| 2005/0238714 A1 | 10/2005 | Rudnic et al. |
| 2005/0256096 A1 | 11/2005 | Combrink et al. |
| 2005/0261262 A1 | 11/2005 | Ma et al. |
| 2005/0277633 A1 | 12/2005 | Ma et al. |
| 2006/0003005 A1 | 1/2006 | Cao et al. |
| 2006/0019985 A1 | 1/2006 | Ma et al. |
| 2006/0019986 A1 | 1/2006 | Ding et al. |
| 2006/0111302 A1 | 5/2006 | Romesberg et al. |
| 2007/0134327 A1 | 6/2007 | Flanner et al. |
| 2008/0132478 A1 | 6/2008 | Flanner et al. |
| 2008/0139526 A1 | 6/2008 | Treacy et al. |

FOREIGN PATENT DOCUMENTS

| | | |
|---|---|---|
| EP | 0293885 | 12/1988 |
| EP | 0436370 | 7/1991 |
| EP | 0652008 | 5/1995 |
| FR | 2585948 | 2/1982 |
| GB | 2087235 | 5/1982 |
| WO | 90/08537 | 8/1990 |
| WO | 94/27557 | 8/1995 |
| WO | 95/20946 | 8/1995 |
| WO | 95/30422 | 11/1995 |
| WO | 96/04908 | 2/1996 |
| WO | 97/22335 | 6/1997 |

| WO | 97/43277 | 11/1997 |
| WO | 98/22091 | 5/1998 |
| WO | 98/46239 | 10/1998 |
| WO | 99/03453 | 1/1999 |
| WO | 99/40097 | 8/1999 |
| WO | 00/48607 | 8/2000 |
| WO | 00/61116 | 10/2000 |
| WO | 01/26663 | 4/2001 |
| WO | 02/38577 | 5/2002 |
| WO | 03/029439 | 4/2003 |
| WO | 2005/056754 | 6/2005 |
| WO | 2005/070941 | 8/2005 |

OTHER PUBLICATIONS

Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6, Mar. 2002, 1686-1691.

Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, 341-347.

Bhargava et al., Pulsed Feeding During Fed-Batch *Aspergillus oryzae* Fermentation Leads to Improved Oxygen Mass Transfer, Biotechnol. Prog. 2003, 19, 1091-1094.

Bhargava et al., Pulsed Addition of Limiting-Carbon During *Aspergillus oryzae* Fermentation Leads to Improved Productivity of a Recombinant Enzyme, Biotechnology and Bioengineering, vol. 82, No. 1, Apr. 5, 2003, 111-117.

Bishai, Comparative Effectiveness of Different Macrolides: Clarithromycin, Azithromycin, and Erythromicin, Johns Hopkins Point of Care Information Technology (POC-IT), posted Dec. 2001.

Bradley, *Staphylococcus aureus* Pneumonia: Emergence of MRSA in the Community, Semin Respir Crit Care Med. 2005; 26 (6): 643-649.

Brogden et al., Cefixirne. A Review of Its Antibacterial Activity. Pharmacokinetic Properties and Therapeutic Potential, Drugs, Oct. 1989; 38 (4): 524-50. (Abstract).

Burgess et al., A Time-Kill Evaluation of Clarithromycin and Azithromycin Against Two Extracellular Pathogens and the Development of Resistance, The Annals of Pharmacotherapy: 1999, vol. 33, No. 12, 1262-1265. (Abstract).

Byfield et al., Relevance of the Pharmacology of Oral Tegafur to its Use as a 5-FU Pro-Drug., Cancer Treat Rep. Jun. 1985; 69 (6): 645-52. (Abstract).

Cappelletty et al., Bactericidal Activities of Cefprozil, Penicillin, Cefaclor, Cefixime, and Loracarbef against Penicillin-Susceptible and Resistant *Streptococcus pneumoniae* in an In Vitro Pharamcodynamic Infection Model, Antimicrobial Agents and Chemotherapy, May 1996, p. 1148-1152.

Cremieux et al., Ceftriaxone Diffusion into Cardiac Fibrin Vegetation. Qualitative and Quantitative Evaluation by Autoradiography, Fundam Clin Pharamcol, 1991; 5(1):53-60. (Abstract).

Endo et al., Fungicidal Action of *Aureobasidin* A, a Cyclic Depsipeptide Antifungal Antibiotic, against *Saccharomyces cerevisiae*, Antimicrobial Agents and Chemotherapy, Mar. 1997, p. 672-676.

Erah et al., The Stability of Amoxycillin, Clarithromycin and Metronidazole in Gastric Juice: Relevance to the Treatment of *Helicobacter pylori* Infection, J Antimicrob Chemother Jan. 1997; 39(1):5-12. (Abstract).

Fang, A Study of the Ethical Considerations and Implications, Prozac Weekly and Sarafem In the Wake of Prozac Patent Expiration, 5.22J/10.02J, Biotechnology and Engineering, 2002.

Freeman et al., The Cyclosporin-Erythromycin Interaction: Impaired First Pass Metabolism in the Pig, Br J Pharmacol, Jul. 1991; 103(3): 1709-12. (Abstract).

Frimodt-Moller, Correlation Between Pharmacokinectic/Pharmacodynamic Parameters and Efficacy for Antibiotics in the Treatment of Urinary Tract Infection, Int. J. Antimicrob. Agents, 19 (2002) 546-53.

Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2002) 51, 101-106.

Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998: 42(8):1996-2001.

Gnarpe et al., Penicillin Combinations Against Multi-Resistant Urinary Pathogens as an Alternative to Gentamycin Treatment, Microbios 1976: 16(65-66):201-6. (Abstract).

Gordon et al., Rationale for Single and High Dose Treatment Regiments with Azithromycin, Pediatric Infectious Disease Journal. 23(2) Supplement: S102-S107, Feb. 2004. (Abstract).

Goswick et al., Activities of Azithromycin and Amphotericin B Against *Naegleria fowleri* in Vitro and in a Mouse Model of Primary Amebic Meningoencephalitis, Antimicrob Agents Chemother. Feb. 2003; 47(2): 524-528.

Harbath et al, Prolonged Antibiotic Prophylaxis After Cardiovascular Surgery and Its Effect on Surgical Site Infections and Antimicrobial Resistance, Circulation Jun. 27, 2000; 101:2916-2921.

Haney, New Drugs Kill Bacteria Resistant to Antibiotics, Called Ketolides, They are Chemically New to the Harmful Bugs, Thursday, Sep. 21, 2000, Seattle Post-Intelligencer.

Harris et al., Esophageal Carcinoma: Curative Treatment, Combined Modalities, The Virtual Hospital, 2004.

Hickey et al., Production of Enterolysin A by a Raw Milk Enterococcal Isolate Exhibiting Multiple Virulence Factors, Microbiology 149 (2003), 655-664.

Hirata et al., Pharmacokinetic Study of S-1, a Novel Oral Fluorouracil Antitumor Drug, Clinical Cancer Research vol. 5, 2000-2005, Aug. 1999.

Hoff et al., Phase I Study with Pharmacokinetics of S-1 on an Oral Daily Schedule for 28 Days in Patients with Solid Tumors, Clinical Cancer Research vol. 9, 134-142, Jan. 2003.

Hoffmann et al., Influence of Macrolide Susceptibility of Efficacies of Clarithromycin and Azithromycin Against *Strepotococcus pneumoniae* in a Murine Lung Infection Model, Antimicrobial Agents and Chemotherapy, Feb. 2003, p. 739-746, vol. 47, No. 2.

Hyde et al., Macrolide Resistance Among Invasive *Streptococcus penumoniae* Isolates, JAMA, Oct. 17, 2001; 288 (15):1857-62. (Abstract).

Iba et al., Comparison Between Continuous Intravenous and Oral Administration of 5-FU with LV, Gan To Kagaku Ryoho. Apr. 1999; 26(5);631-5. (Abstract).

Klugman, Bacteriological Evidence of Antibiotic Failure in Pneumococcal Lower Respiratory Tract Infections, Eur Respir J 2002; 20 Suppl, 36, 3s-8s.

Kramer et al., Statistical Optimisation of Diclofenac Sustained Release Pellets Coated with Polymethacrylic Films, Int J Pharm. Apr. 30, 2003; 256(1-2):43-52 (Abstract).

Laine et al., Frequency and Clinical Outcome of Potentially Harmful Drug Metabolic Inteactions in Patients Hospitalized on Internal and Pulmonary Medicine Wards: Focus on Warfarin and Cisapride, Therapeutic Drug Monitoring. 22 (5):503-509, Oct. 2000. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509. 2000.

Lamb et al., Ceftriaxone: An Update of its Use in the Management of Community-Acquired and Noscocomial infections, Drugs. 2002:62(7):1041-89. (Abstract).

Lerner-Tung et al., Pharmacokinetics of Intrapericardial Administration of 5-Fluorouracil, Cancer Chemother Pharmacol. 1997; 40(4):318-20. (Abstract).

Lin et al., Multiple-Dose Pharmacokinetics of Ceftibuten in Healthy Volunteers, Antimicrobial Agents and Chemotherapy, Feb. 1995, p. 356-358.

Lindsey et al., Extraction of Antibiotics From Agricultural Wastewater, USGS, 220th ACS Meeting Washington, D.C.; Aug. 20-24, 2000. (Abstract).

Livermore et al., Activity of Ertapenem Against *Neisseria gonorrhoeae*, Journal of Antimicrobial Chemotherapy 2004 54(1):280-281.

Marten et al., Monthly Report, Jul. 2004, Pulsatile Dosing of Antifungal Compounds, UMBC; to Dr. Robert J. Guttendorf, Advancis Pharmaceutical Corp.

Mazzei et al., How Macrolide Pharmacodynamics Affect Bacterial Killing, Infect Med 16(sE)22-28, 1999. (Abstract).

Nightingale, Pharmacokinectics and Pharmacodynamics of Newer Macrolides, Pediatric Infectious Disease Journal. 16(4):438-443, Apr. 1997. (Abstract).

Olofinlade et al., Anal Carcinoma: A 15-Year Restrospective Analysis, Scand J Gastroenterol 2000:35; 1194-1199.

Parmar-Lapasia et al., A Comparison of Two Macrolide Antibiotics in the Treatment of Community-Acquired Infections, P & T (Pharmacy & Therapeutics), Oct. 2003, vol. 28, No. 10.

Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 (Nov. 15) 2001: 4267-4269.

Polak. Pharmacokinetics of Amphotericin B and Flucytosine, Postgrad Med J. Sep. 1979: 55(647):667-70. (Abstract).

Porter et al., Antibiotics and Infectious Diseases in Otolaryngology—HNS, Grant Rounds Presentation, UTMB, Dept. of Otolaryngology, May 8, 2002.

Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.

Ranga Rao et al., Influence of Molecular Size and Water Solubility of the Solute on its Release from Swelling and Erosion Controlled Polymeric Matrices, Journal of Controlled Release, 12 (1990) 133-141.

Reza et al., Comparative Evaluation of Plastic, Hydrophobic and Hydrophilic Polymers as Matrices for Controlled-Release Drug Delivery, J. Pharm, Pharmaceut. Sci., 6(2):282-291, 2003.

Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother. May 1990; 34(5):909-10. (Abstract).

Rivkees et al., Dexamethasone Treatment of Virilizing Congenital Adrenal Hyperplasia: The Ability to Achieve Normal Growth, Pediatrics 2000; 106; 767-773.

Roblin et al., In Vitro Activity of a New Ketolide Antibiotic; HMR 3647, Against Chlamydia Pneumoniae, Antimicrob Agents Chemother. Jun. 1998; 42(6): 1515-15116.

Santini et al., The Potential of Amifostine: From Cytoprotectant to Therapeutic Agent, Haematologica Nov. 1999; 84(ii): 1035-1042.

Sanz et a., Cefepime Plus Amikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.

Schweizer et al., "Single Shot" Prevention in Abdominal Surgery, Antibiotics with Long Half-Life (Cefriazone, Omidazole) vs. Antibiotics with Short Half-Life (Cefazolin, Metronidazole, Clindamycin), Helv Chir Acta. Apr. 1994; 60 (4):483-8. (Abstract).

Shvartzman et al., Treatment of Streptococcal Pharyngitis with Amoxycillin Once a Day, BMJ vol. 306, pp. 1170-1172, May 1, 1993.

Stringer et al., Section 3: Diseases of the Ear, Part 4: Inner Ear, Chapter 46: Ototoxicity, Paparella: vol. II, Otology and Neuro-Otology, W B. Saunders Co., 3rd Edition, 1990.

Suda et al., The Synthesis and In Vitro and In Vivo Stability of 5-Fluorouracil Prodrugs Which Possess Serum Albumin binding Potency, Biol Pharm Bull. Sep. 1993;16(9):876-7. (Abstract).

Sandip et al., Controlled Release Formulation of Tramadol Hydrochloride Using Hydrophillic and Hydrophobic Matrix System, AAPS PharmSciTech 2003; 4(3) Article 31.

Waters, Colorectal Cancer-Drug Treatment, Hospital Pharmacist, vol. 11, pp. 17-192, May 2004.

Wattenberg, Prevention of Carcinogenesis of the Respiratory Tract by Chemopreventive Agents Delivered by Aerosol, International Society of Cancer Chemoprevention, vol. 1, No. 6, Jan. 2003.

Whitehead et al., Amoxycillin Release From a Floating Dosage Form Based on Alginates, International Journal of Pharmaceutics 210 (2000) 45-49.

Yousef et al., Combined Action of Amoxycillin and Dicloxacillin Against *Staphylococcus aureus* In Vitro, Pharmazie Sep. 1985; 40(9):650-1, (Abstract).

About Macrolides, About That Bug.com (2006).

Amoxycillin (As Trihydrate), Moxyvit (2003).

Amoxicillin + Clavulanate, PetPlace.com (2005).

Answers.com, Macrolide (2006).

Antimetabolites, GPnotebook (2005).

Augmentin, Product Information, GiaxoSmithKline, Physicians Desk References, Jun. 2004, pp. 1421-1433.

Augmentin XR (PDR entry for) (GlaxoSmithkline), (Amoxicillin/Clavulanate Potassium), Extended Release Tablets, Jun. 2004.

Beta Lactam Antibiotics, Health 24.com (2005).

Biaxin XL, Once-Daily Biaxin XL Clarithromycin Extended-Release Tablets, Abbott Laboratories Online (2004).

Biaxin XL, Once-daily, Clarithromycin Extended-Release Tablets (2005).

Biaxin Filmtab, Biaxin XL Filmtab, Biaxin Granules, pp. 1-25, Abbott Laboratories (2005).

Body Chemistry, Acid Alkaline Foods, Acid Reflux? Gas, Acid Indigestion, Acid/Alkaline Balance, Printed from timberware.com/chemistry.html on Jan. 2, 2012.

Citizen Petition, McNeil Consumer & Specialty Pharmaceuticals, Mar. 19, 2004.

Clarithromycin Extended-Release Scientific Posters Presented to the 39th Interscience Conference on Antimicrobial Agents and Chemotherapy (ICAAC). San Francisco, Sep. 26-29, 1999.

Clearance and the Elimination Rate Constant, Ke (Elimination Rate)—Half-Life, Oct. 14, 2002.

Complementary Medicine Saves Money, Medicine, Greenhealthwatch.com, Collection of medical headlines citing to sources dated between May 1, 1997 and Aug. 10, 2002.

Dispensing Errors With Depakote, New Formulation Creates Confusion, Patient Safety, Practitioners Reporting News, USP Issued Mar. 3, 2001.

Drugs.com, Drug information for Diclofenac (Topical) (2006).

Drug, Bio-Affecting and Body Treating Compositions (Class 424), 475 Sustained or differential release, United States Patent and Trademark Office, Classification Definitions as of Jun. 30, 2000.

Elimination Rate Constant/Half-Life, Ke (Elimination Rate)—Half-Life, Oct. 14, 2002.

Emulsions, Secundum Artem, vol. 4, No. 1, printed from www.padocklabs.com/html/resource/pdf/sed Artem 4.1.pdf on Jan. 2, 2012.

Encyclopedia Britannica Online, Types of Drugs>Antimicrobial Drugs>Antibiotics>Macrolides, Mar. 28, 2006.

Excenel, Swine Health Management, Prewean Program. Pfizer Salud Animal (2005).

Fabrication of Metronidazole Strips, 996 Die Pharmazie 50(1995) February, No. 2.

Food and Drug Administration Center for Drug Evaluation and Research Approved Drug Products With Therapeutic Equivalence Evaluations, 24th Edition, Feb. 26, 2004.

Getting a Drug into the Body: Absorption, from How Drugs Work: Basic Pharmacology for Healthcare Professionals, Hugh McGarock, 2nd Edition, May 2005.

Highlights on Antineoplastic Drugs, Pharmacia, vol. 11, No. 4, 1993.

Jock Itch and Other dermatophytes. Mycolog.com (Sep. 2002).

Klarithran Ranbaxy(SA)(PTY) Ltd, Jun. 2005.

Klucel Hydroxypropyicellulose (HPC). Hercules Incorporated (2004).

Bahnmuller, Metabolites of Microorganisms. 248. Synthetic Analogs of Saphenamycin, J. Antibiot (Tokyo). Nov. 1988; 41(11): 1552-60.

Borman, Chemistry Highlights 2005, Chemical & Engineering News, Dec. 19, 2005, vol. 83, No. 51, pp. 15-20.

Bradley, *Staphylococcus aureus* Pneumonia: Emergence of MRSA in the Community, Semin Respir Crti Care Med. 2005; 26(6): 643-649.

Cirz et al., Inhibition of Mutation and Combating the Evolution of Antibiotic Resistance, PLOS Biology, Jun. 2005, vol. 3, Issue 6, e176, pp. 1024-1033.

Darst, New inhibitors Targeting Bacterial RNA Polymerase, Trends in Biochemical Sciences, vol. 29, No. 4, Apr. 2004, pp. 159-162.

Dellit, M.D., Tim, University of Washington and Infectious Diseases Society of Washington; Jeffrey Duchin, MD, Public Health—Seattle & King County and University of Washington; Jo Hofmann, MD, Washington State Department of Health and University of Washington; Erika Gurmai Olson, MD, Tacoma-Pierce County Health Department Antibiotic Resistance Task Force, Interim Guidelines for Evaluation and Management of Community-Associated Methicillin-Resistant *Staphylococcus aureus* Skin and Soft Tissue Infections in Outpatient Settings. Sep. 2, 2004.

Geiger et al., Metabolites of Microorganims. 247. Phenazines from Streptomyces Antibiotics, Strain Tu 2706, J Antibiot (Tokyo). Nov. 1988; 41 (11): 1542-51.

Gorwitz, et al., Strategies for Clinical Management of MRSA in the Community: Summary of an Expert's Meeting Convened by the Centers for Disease Control and Prevention, Department of Health and Human Services Centers for Disease Control and Prevention, Mar. 2006.

Henry, Disabling Resistance Inhibiting Key Proelase Prevents Bacteria From Evolving Drug Resistance, Chemical and Engineering News, May 16, 2005, vol. 83, No. 20, p. 8.

Johnson, N.J. Experts Urge Prudent Antibiotic Use, Examiner.Com, The Associated Press, Jul. 31, 2006.

Kitahara, et al., Saphenamycin, A Novel Antibiotic From a Strain of Streptomyces, J. Antibiot (Tokyo). Oct. 1982; 35 (10):1412-14.

Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).

Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.

Berry et al., Bacteriological Efficacies of Three Macrolides Compared with Those Amoxicillin-Clavulanate Against *Streptococcus pneumoniae* and *Haemophilus influenzae*, Antimicrob Agents Chemother. Dec. 1998; 42(12): 3193-3199.

Cha et al., Pulsatile Delivery of Amoxicillin Against *Streptococcus pneumoniae*, Journal of Antimicrobial Chemotherapy, Advance Access Published Oct. 14, 2004.

Craig, Antibiotic Selection Factors and Description of a Hospital-Based Outpatient Antibiotic Therapy Program in the US, Eur J .Clin Microbial Infect Dis. Jul. 1995: 14(7):636-42. (Abstract).

Feder et al., Once-Daily Therapy for Streptococcal Pharyngitis With Amoxicillin, American Academy of Pediatrics, vol. 103(1), Jan. 1999, pp. 47-51.

Hoffman et al., Pharmacodynamic and Pharmacokinetic Rationales for the Development of an Oral Controlled-Release Amoxicillin Dosage Form, Journal of Controlled Release 54 (1998) 29-37.

Mainz at al., Pharmacokinetics of Lansoprazole, Amoxicillin and Clarithromycin After Simultaneous and Single Administration, Journal of Antimicrobial Chemotherapy (2002) 50, 699-706.

Todar's Online Textbook of Bacteriology, Antimicrobial Agents Used in Treatment of Infectious Disease, 2002 Kenneth Todar University of Wisconsin-Madison Department of Bacteriology.

Vanderkooi et al., Antimicrobial Resistance and the *pneumococcus*, Infectious Diseases and Microbiology, vol. 3, Issue 5, May 2004.

Declaration of Michael J. Ryback. from the prosecution of U.S. Appl. No. 09/792,092; Sep. 23, 2002.

Five vs. 10 Days of Therapy for Streptococcal Pharyngitis, American Family Physician, Feb. 15, 2001.

Meeting the Challenge of a New Generation of Respiratory Pathogens, MAC (2001).

MedicineNet.com Generic Name: Acyclovir, Brand Name: Zovirax, Dec. 31, 1997.

The Merck Index, An Encyclopedia of Chemicals, Drugs, and Bioogicals, Twelfth Edition, pp. 397-398 (1996).

Methods of Formulation Controlled Release Products Outside of the Claims of Forest Laboratory Patents U.S. 4,369,172 and U.S. 4,389,393, Technical Information Dow Chemical Feb. 1991.

Miconazole, The Merck Index Results—Form view, Monograph No. 06202 (2005).

Mode of Action of Macrolides in Blocking Translation During Bacterial Protein Synthesis: Blocking Peptidyltransferase. Doc Kaiser's Microbiology Home Page, Oct. 13, 2004.

Module 8—Therapeutics. May 25, 2002, Newcastle. BPAIIG Immunology/Infectious Diseases Training Programme, Module: Therapeutics.

Monistat, Which Treatment is Right for You?, Vaginal vs. Oral Therapy (2004).

Neisseria Meningitidis, The Doctor's Doctor, Nov. 8, 2004.

New-Generation Aromatase Inhibitor for Breast Cancer: Anastrozole Challenges Tamoxifen in First-Line Therapy, 10th European Cancer Conference (ECCO 10), Vienna, Austria/Sep. 12-16, 1999.

New Product Newswire, Drug Topics Archive, Aug. 5, 2002.

Nitrofurantoin, Eckerd Prescription Advisory, Feb. 15, 2001.

Nursing, Cancer Nursing; Principles and Practice, Fifth Edition, Jones and Barlett Publishers, 2000.

Oral Capecitabine Should Improve Convenience of Chemoradiation for Locally Advanced Rectal Cancer—New Treatment Appears to be Safe and Effective, PeerView Press, Chemotherapy (ICAAC), Sep. 27-30, 2002; San Diego, CA, 40th Annual Meeting of Infectious Diseases Society.

Oral Extended (Controlled) Release Dosage Forms, In Vivo Bioequivalence and In Vitro Dissolution Testing, Office of Generic Drugs (1993).

Pharmaceuticals, Pharmacos Unit F2 Pharmaceuticals V 6.0, Eudralex Collection 3AQ19a 1992.

Physicians Desk Reference, PDR 57 Edition 2003, p. 402/Abbott.

Principles of Diagnosis of Infectious Diseases and Antimicrobial Therapy, Antibiotic Guideline, Dr. Norman Miller et al., 2nd Edition, Chapters 1-3, printed from www.sassit.co.za/Journal/Infections/Antibiotics/Middes/AntibioticGuide/pdf printed on Jan. 2, 2012.

Procardia XL (Nifedipine) Extended Release Tablets for Oral Use, 69-4467-00-8, Pfizer Labs, Aug. 2003.

Summary of Product Characteristics, Doxycycline Capsules BP 50mg, Nov. 2001.

Sustained or Differential Release Type, USPTO Classification Definitions (Dec. 2002 Edition) 964.

Sustained-Release Dosage Forms, Degussa, Rohm Pharma Polymers, printed from www.solimide, eu/en/pharmapolymers/service/literature/practical_course.Par.0001.TROW.0010.Tcell.0003.File, tmp/pc_30_sustained.pdf on Jan. 2, 2012.

Testicular Cancer: Questions and Answers, Cancer Facts, National Cancer Institute, Aug. 14, 2003.

Traditional Chemotherapy, Chapter 25 from Prevention and Therapy of Cancer and Other Common Disease: Alternative and Traditional Approaches; Infomedix 1996.

* cited by examiner

Figure 1. Penicillin VK Eradication Rate vs Total T>MIC

Figure 2. Contour Plot from GLM

PHARMACEUTICAL COMPOSITIONS AND METHODS FOR IMPROVED BACTERIAL ERADICATION This application claims the priority of U.S. Provisional Application Ser. No. 60/798,109, filed May 5, 2006.

This invention is directed to compositions and methods for improving the efficacy of time-dependent antibiotics when used in the treatment of humans or animals having bacterial infections. As used herein the term "time-dependent antibiotic" shall denote those antimicrobial compounds in general, and antibiotics in particular, having an efficacy that is believed to be more dependent on the daily time that the compound's concentration is above the minimum inhibitory concentration (MIC) rather than the number of multiples of that MIC achieved. Non-limiting examples of examples of such time-dependent antibiotics shall include the penicillins, the beta-lactams, the cephalosporins, and the carbapenams. This invention is particularly directed to compositions and methods for improving the efficacy of beta-lactam antibiotics when used in the treatment of humans or animals having bacterial infections. This invention is more particularly directed to compositions and methods for improving the efficacy of amoxicillin and cephalexin when either is used in the treatment of humans or animals having bacterial infections.

In the bacterial infection treating discipline it has been widely accepted that the efficacy of any given dosing regimen utilizing a time-dependent antibiotic is founded upon achieving and/or maintaining a minimum inhibitory concentration (MIC) of the time-dependent antibiotic (not bound to serum proteins) for a certain minimum percentage of time in a day (i.e. a Daily T>MIC). (See Auckenthaler R, *Pharmacokinetic and pharmacodynamics of oral beta-lactam antibiotics as a two-dimensional approach to their efficacy*; J Antimicrob Chemother. 2002 July; 50 Suppl: 13-7). (See also Vanderkooi O, Low D, *Antimicrobial Resistance and the Pneumococcus*, Infectious Diseases and Microbiology Rounds, May 2004, Vol. 3, Issue 5).

The instant invention provides both new and improved therapeutic paradigms and products for use with a given time-dependent antibiotic against a given bacterial pathogen having a known, or determinable, MIC for the given (or predictably similar acting) time-dependent antibiotic, which paradigms and products are derived from Applicants' development of a unique model parameter. This model parameter may serve as a more accurate barometer for predicting the efficacy of a given dosing regimen than has the prior art's heretofore and enduring focus on daily T>MIC.

Figure 1:
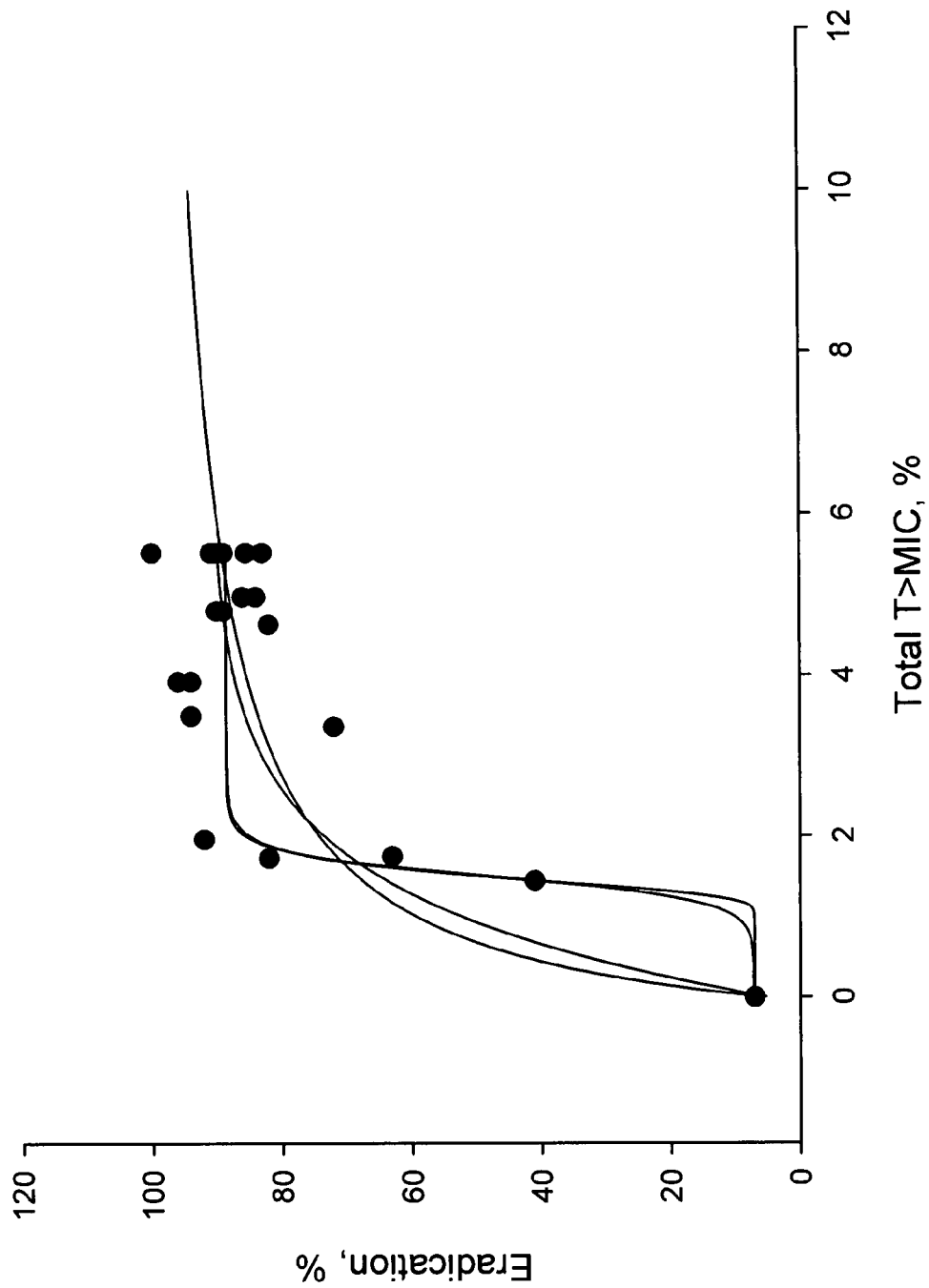
FIG. 1 is a plot showing penicillin VK eradication rate versus Total T>MIC for four different model fits of data.

In accordance with an aspect of the present invention, there is provided a product and treatment regimen for use of a time-dependent antibiotic for treating a bacterial infection, in which the treatment is based on achieving a Total T>MIC to achieve a desired result, generally a percent eradication (or clinical outcome) of the bacterial pathogen that causes the infection.

The course of treatment may be determined for a specified dosage of antibiotic and for the MIC of the bacteria being treated by such antibiotic.

Based on PK data for the antibiotic of interest (or a closely related antibiotic) and the specified dosage, the daily time over MIC is determined.

In addition, based on actual treatment data (e.g., clinical trial data) for such antibiotic (or closely related antibiotic) there is determined the percent eradication (or clinical cure rate) of the bacteria over the specified course of treatment at a specified dosage.

By using (1) the daily time over MIC (Daily T>MIC) determined from the PK data and (2) the percent eradication (or clinical cure rate) over the course of treatment reported in the actual treatment, the total time over MIC (Total T>MIC) that achieved the bacterial eradication (or clinical cure rate) can be determined.

Such data is then plotted and art-recognized techniques may be used to establish an equation based on the data.

By way of mathematical and statistical modeling Applicants calculated the actual pharmacokinetic (PK) curves from the data from their own failed amoxicillin Phase III Trial against *Streptococcus pyogenes*, and from the data of published studies. Those published studies used various dosing regimens of penicillin VK also against *Streptococcus pyogenes*. This modeling led to Applicants' novel finding that duration of the dosing regimen is a statistically important factor in the bacterial eradication rate.

From those actual pharmacokinetic curves Applicants have developed their model parameter that takes dosing regimen duration into account as a determinant of bacterial eradication, while providing an excellent fit to the (PK) data of Applicants own failed amoxicillin Phase III Trial and to the (PK) data of the literature Applicants surveyed. Applicants have termed this novel treatment duration-encompassing model parameter as "Total T>MIC," which they define by the general equation:

Total $T>MIC$=Daily $T>MIC$×Duration of Dosing Regimen

Thus, the Total T>MIC parameter includes both Daily T>MIC and Duration in a single parameter that provides a better model and explanation of the eradication rate of various regimens than either Daily T>MIC or Duration alone.

In accordance with one aspect of the method of the instant invention actual pharmacokinetic (PK) data is used to determine the concentration in serum of a drug at a given dosage, so as to further determine the Daily T>MIC provided by the drug at that given dosage. Studies reported in the literature are then consulted to determine the number of days that the drug was used at that given dosage to obtain a percent eradication. Based on the number of days of duration and the PK data, Applicants have found that they can then calculate the Total T>MIC that provides that percent eradication.

The data necessary for a determination of this modeling parameter such as drug, regimen, Days Tx, and Eradication are culled from the studies published in the literature, or otherwise known to the formulation artisan from clinical trials or similar sources. Table 1 is a compilation of a portion of the data from the various penicillin VK/*Streptococcus pyo-* genes studies that the Applicants utilized to calculate the actual pharmacokinetic curve and to develop the Total T>MIC model parameter.

derived from the dosing regimen or clinical trial studied and/or reported in the literature. For example, some of the data in FIG. 1 is presented in tabular form in Table 1 above.

TABLE 1

| Drug | Regimen | MIC-90 | Daily T > MIC | Days Tx | % Erad | Total T > MIC | Ref |
|---|---|---|---|---|---|---|---|
| Pen VK | 500 TID | 0.015 | 48.10% | 0 | 7 | 0 | Zwart et al, BMJ 2000 |
| Pen VK | 500 TID | 0.015 | 48.10% | 3 | 41 | 1.443 | Zwart et al, BMJ 2000 |
| Pen VK | 500 TID | 0.015 | 48.10% | 7 | 72 | 3.367 | Zwart et al, BMJ 2000 |
| Pen VK | 500 TID | 0.015 | 48.10% | 10 | 89 | 4.81 | Ketek SBA; Norrby et al, Scand J Infect Dis 2001 |
| Pen VK | 600 TID | 0.015 | 49.80% | 10 | 86 | 4.98 | Carbon et al, J Antimicrob Chemother 1995 |
| Pen VK | 250 QID | 0.015 | 55.30% | 10 | 100 | 5.53 | McCarty 1993 |
| Pen VK | 250 QID | 0.015 | 55.30% | 10 | 85.5 | 5.53 | Mullen 992 |
| Pen VK | 250 QID | 0.03* | 46.40% | 10 | 82 | 4.64 | Omnicef label; Tack et al, AAC 1998 |
| Pen VK | 250 TID | 0.015 | 39.29% | 10 | 96 | 3.929 | Gerber et al, AJDC 1987 |
| Pen VK | 250 TID | 0.015 | 39.29% | 5 | 92 | 1.9645 | Gerber et al, AJDC 1987 |
| Pen VK | 800 BID | 0.015 | 35.00% | 10 | 94 | 3.5 | Stromberg et al, Scand J Infect Dis 1988 |
| Pen VK | 800 BID | 0.015 | 35.00% | 5 | 73 | 1.75 | Stromberg et al, Scand J Infect Dis 1988 |
| Pen VK | 750 QD | 0.015 | 17.30% | 10 | 82 | 1.73 | Gerber et al, AJDC 1989 |

BRIEF DESCRIPTION OF THE SEVERAL VIEWS OF THE DRAWINGS

FIG. 1 shows four different model fits of data a portion of which is shown in Table 1 wherein % bacterial eradication is expressed as functions of Total T>MIC.

Figure 2:
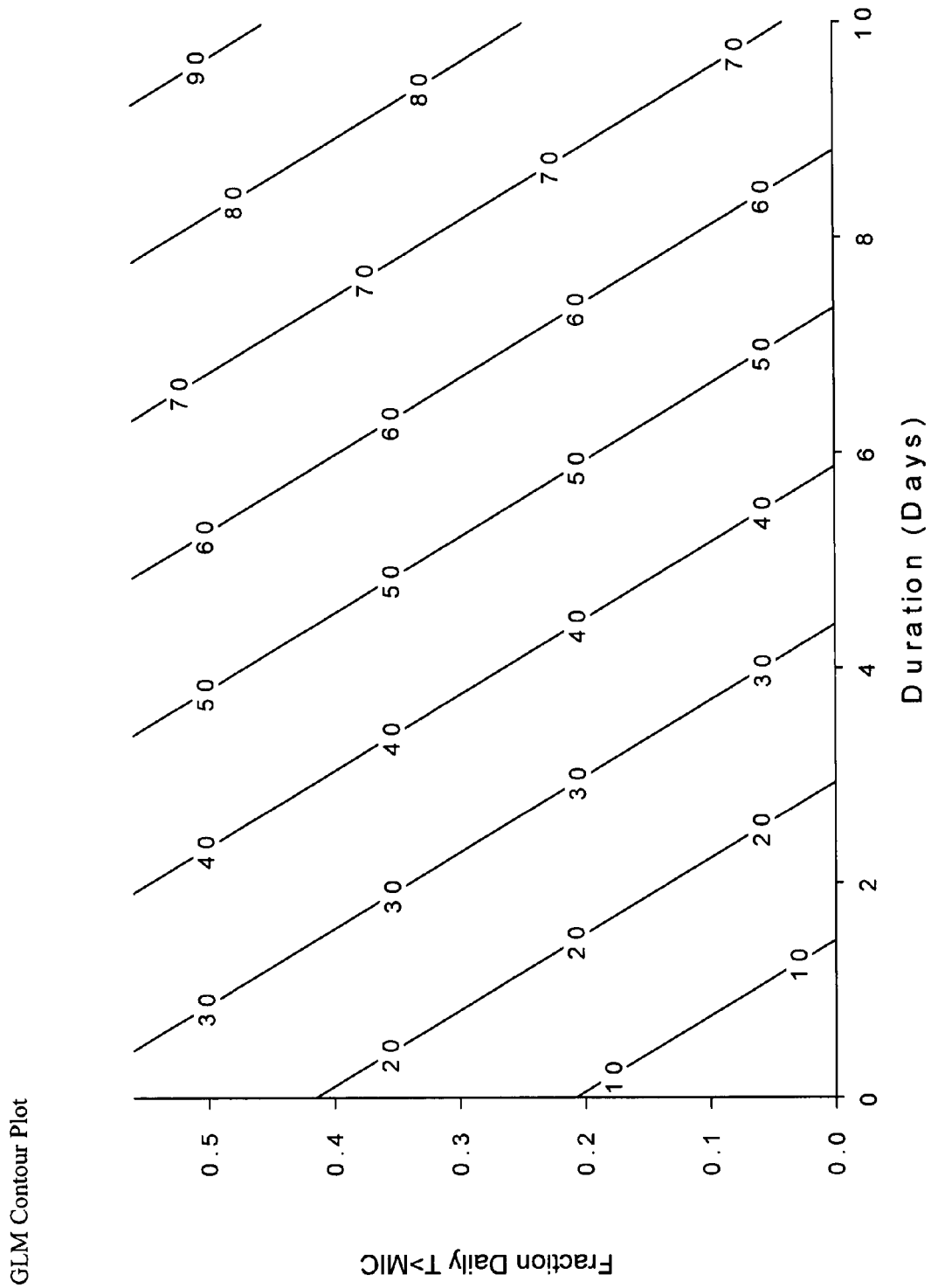
FIG. 2 is a contour plot of the response surface from the GLM model for the data shown in FIG. 1.

FIG. 2 shows a contour plot of the response surface from the GLM approach (discussed in Example 2) for the data shown in FIG. 1.

FIG. 1 shows four different model fits of data a portion of which is shown in Table 1 wherein % bacterial eradication is expressed as functions of Total T>MIC. FIG. 1 also graphically illustrates how the model may be used to select regimens having adequate doses (which relate to the Daily T>MIC) and sufficient Durations (more importantly), so as to achieve desired eradication of *Streptococcus pyogenes*, or desired eradication of other infectious microbial species that have been similarly studied in existing literature and/or clinical trials, or that may be similarly studied in future literature and/or clinical trials.

It should be understood that in accordance with the invention, the model parameter, Total T>MIC, can be accurately related to the observed eradication of various regimens through various mathematical equations and functions. For the data presented in FIG. 1 either a simple Emax model or a sigmoid Emax model can provide an adequate fit. However, in accordance with the invention there are manifold mathematical models and relationships that can be used to provide an adequate relationship of Total T>MIC to % Eradication, as is demonstrated by the four different model fits shown in FIG. 1. One of ordinary skill in the art of PK/PD modeling will select which model is appropriate for the given data set depending on his experience, the type and origin of the data, and a variety of statistical measures such as akaike information criterion, root mean square error, $r^2$, residual analysis, and others. The artisan of ordinary skill in PK/PD modeling will appreciate that very often more than one mathematical model form can provide an adequate fit.

Example 1

Total T>MIC in a Simple Emax Model or Sigmoid Emax Model

Determination of the Total T>MIC parameter requires two separate terms, Duration and Daily T>MIC. Both of these are The information in Table 1 was collected from several studies published in the literature. Information such as drug, regimen, Days Tx and Eradication can be taken directly from the literature articles. Information such as the MIC will often have been determined as part of the study and may be reported in the article, but in many cases it may not have been determined or reported. In those cases wherein the MIC was not determined and reported Applicants assumed that the MIC was equal to 0.015 μg/mL, the MIC determined in the Phase III Clinical Trial conducted by Applicants.

The Daily T>MIC must also be calculated for each different regimen, and at the relevant MIC. This information was not presented in any of the articles and so it was calculated by Applicants. The Daily T>MIC is calculated for each regimen by creating a plasma profile from pharmacokinetic data published in the literature. Prior to creating the plasma profile a pharmacokinetic model is developed from plasma profiles from one or more doses reported in the literature. The PK model is first checked for accuracy against the profiles used in the derivation of the model and then the PK profile of regimens for which actual plasma data do not exist are simulated so that the Daily T>MIC may be calculated. The models are industry standard compartmental models, generated with WinNonlin, a common program used in the pharmaceutical industry for pharmacokinetic analysis and modeling.

Once the Daily T>MIC for each regimen has been calculated, the Total T>MIC is calculated by multiplying the Daily T>MIC by the Duration of Therapy (Days Tx in the table). Thus a composite parameter, Total T>MIC, is constructed that includes both factors relevant to eradication of *Streptococcus pyogenes* by a given regimen. The equation can then be used to determine the Total T>MIC required to achieve eradication rates ≧85% (or any other desired eradication rate).

Penicillin and amoxicillin are both beta-lactam antibiotics and have the same mechanism of action against *Streptococcus pyogenes*. Therefore, the pen VK Total T>MIC model can be applied to assist in the prediction or selection of the appropriate dosing regimen of amoxicillin Pulsys™. The Pulsys™ technology is illustrated in U.S. Pat. No. 6,544,555, the disclosures of which are hereby incorporated by reference in their entireties. Applicants found that when the Daily T>MIC of Applicants' once-daily 775 mg tablets and the clinical trial's 7 day dosing Duration were plugged into the Total T>MIC model the predicted eradiation rate was 87%. The actual eradication rate was 77% thus the prediction is within the error of the model.

In order to determine the optimum dose and duration of amoxicillin Pulsys™ the Daily T>MIC of amoxicillin was obtained from pharmacokinetic studies conducted by Applicants on various amoxicillin Pulsys™ formulations. Bearing in mind that it is desirable from therapy compliance, convenience, and marketing perspectives to keep the duration of a dosing regimen to 10 days or less, Applicants selected a formulation that provided a Daily T>MIC that when multiplied by 10 days of Duration exceeded the Total T>MIC corresponding to an 85% (actually 90% was used to provide a margin of error) eradication rate.

Emax is a typical model used to describe pharmacodymic relationships between a parameter of interest and a pharmacodynamic effect. Illustrating an aspect of the instant invention a simple Emax model provides an excellent relationship between the Total T>MIC parameter and the eradication rate.

In accordance with an aspect of one embodiment of the instant invention a simple Emax model takes the following mathematical form:

$$E = E0 + (Emax - E0)*(\text{Total } T{>}MIC/(\text{Total } T{>}MIC + \text{Total } T{>}MIC50)$$

wherein,

E is the % eradication, these values are taken from the reference data set;

E0 is the % eradication at Total T>MIC of 0, i.e. spontaneous eradication or placebo effect;

Emax is the maximum eradication, set to a constant 100% in the model;

Total T>MIC is the parameter calculated by multiplying daily T>MIC times the number of days the product was administered; and Total T>MIC50 is a fitted parameter that corresponds to Total T>MIC where E=50%.

In development of the above equation for a given set of reference literature data, a computer program such as WinNonlin, Statgraphics, SigmaPlot, SAS, JMP, Excel or other modeling software is employed to fit the parameters E0 and Total T>MIC50. For the data in FIG. 1 the fitted Emax model was determined to be:

$$\% \text{ Eradication} = 5.75 + 94.3 * \text{Total } T{>}MIC/(\text{Total } T{>}MIC + 0.74)$$

This equation can now be utilized to solve for the optimum duration to achieve a given eradication rate. This is especially useful for developing novel products, because once the daily time above MIC of the novel product is determined, the number of studies required to determine an effective dosing regimen can be greatly reduced, thus saving valuable time to market and clinical study costs. It is to be understood that the constants of the hereinabove equation will vary depending on the drug formulation that is used.

Example 2

General Linear Modeling Methodology

As earlier noted, alternative modeling methodologies may also be employed in practicing the instant invention. One such method is termed general linear modeling (GLM) and is a common method for developing models that include multiple variables. The advantage of GLM is that each of the important variables, Duration and Daily T>MIC, are modeled independently and do not have to be combined into a single composite factor. In application of the GLM with 2 variables (Duration and Daily T>MIC) the data are handled in 3 dimensions, instead of 2 as for the Total T>MIC case. This can lead to a greater understanding of the relationship between Duration and Daily T>MIC, and detection of possible synergistic effects not detected in the single variable model. To illustrate this two dosing regimens may be considered, wherein Formulation A provides 100% Daily T>MIC and is administered for 5 days thereby providing a Total T>MIC of 5 days; and wherein Formulation B provides 50% Daily T>MIC and is administered for 10 days thereby providing a Total T>MIC of 5 days. There is no guarantee that the eradication rate from both regimens would be equivalent, but the Total T>MIC model would predict them to be equivalent. The GLM model would have two different points on a 3 dimensional surface for the two regimens in question, thus the GLM model is able account for effects not detectable in the single parameter Total T>MIC model. In fact, the synergy term in the GLM is actually the Total T>MIC parameter. A contour plot of the response surface from the GLM approach for the data shown in FIG. 1 is provided below in FIG. 2.

Succinctly, GLM is a statistical modeling approach based on the determination of significant factors in a data set, and finding coefficients to those factors that fit the data. A benefit of this type of approach when used for the data in FIG. 1 is that it breaks the Total T>MIC into its component parts, daily T>MIC and Duration, and weights each according to the data. Total T>MIC may also be included in the model as an interaction term if it is determined be a significant factor. In this approach there is no specific model form as there is with the Emax model: the model form is based on the analysis of data and can take many forms such as a simple linear or complex polynomial form. Typically a statistical software package, such as Statgraphics, SAS, JMP, Statistica, or Minitab is used to develop a GLM. For the data in FIG. 1 a general linear model approach yielded the following equation:

$$\% \text{ Eradication} = 6.81 * \text{Duration} + 0.48 * \text{Daily } T{>}MIC$$

wherein,

% Eradication is the eradication rate;

Duration is the number of days the dose is administered; and

Daily T>MIC is the percent T>MIC per day provided by the dose regimen.

The GLM equation may now be solved as the Emax model above to derive the optimum duration given a T>MIC or the required daily T>MIC for a known duration. This model approach provides an improved ability to fit effects that are dependent upon more than one factor. The Total T>MIC is such a parameter because it is actually made up of two factors, duration and daily T>MIC. The GLM provides a means to generate different eradication rates in the case where two regimens provide the same Total T>MIC, such as when a product with 50% daily T>MIC is administered for 10 days versus a product with a 100% daily T>MIC administered for 5 days.

FIG. 2 illustrates the strong effect of Duration on % eradication. Relative changes in Duration increase % eradication more than the same magnitude of change in Daily T>MIC. To Applicants' knowledge this effect has never been disclosed previously and is the basis for changing the amoxicillin Pulsys™ regimen from 7 days to 10 days.

Example 3

Modified Multiple Parameter Emax

One potential limitation of the GLM approach is that in the case of lower order models there is a potential for the predicted effect to go above the maximum allowable effect, e.g.

100% eradication. In order to overcome this limitation, the inventors have modified the simple Emax model to be able to incorporate more than just the Total T>MIC term. This improved equation provides the ability to model each important term in the data set, Duration, Daily T>MIC and Total T>MIC, thus best fitting each data point in the appropriate factor space, but adding the maximum effect limitation, e.g. 100% eradication. The equation has the same form as the simple Emax model, except that the Total T>MIC50 term is changed to a term that incorporates the Duration and the Daily T>MIC, as shown below:

$$E=E0+(Emax-E0)*(\text{Total } T>MIC)/(\text{Total } T>MIC+(a+b*\text{Duration}+c*\text{Daily } T>MIC))$$

wherein,

E=Eradication rate, expressed here as a fraction not as percent in this model;

E0 is the fraction eradicated at a Total T>MIC of 0, i.e. spontaneous eradication or placebo effect;

Emax is the maximum eradication, set to a constant of 1.0 (representing 100% in this model);

Total T>MIC is the parameter calculated by multiplying daily T>MIC times the number of days the product was administered;

Duration is the number of days the dose is administered;

Daily T>MIC is the fraction T>MIC per day provided by the dose regimen; and a, b, and c are coefficients determined during the fitting of the reference data.

In development of the above equation for a given set of reference literature data, a computer program such as Statgraphics, SigmaPlot, SAS, JMP, Excel, or other modeling software is employed to fit the parameters E0, a, b, and c. For the data in FIG. 1 the fitted model was determined to be:

$$\text{Fraction Eradicated}=0.058+0.942*\text{Total } T>MIC/(-2.99+0.316*\text{Duration}+10.94*\text{Daily } T>MIC)$$

This equation may now be utilized to determine the optimum Duration of a novel therapy provided the daily T>MIC is known or vice versa. The equation developed here can maintain the maximum effect below the 100% limit, and, unlike the simple Emax model, can fit individual points with a common Total T>MIC but, different duration or daily T>MIC, that may lead to different eradication rate because of the response to duration and daily T>MIC, can be different.

Each of the three different approaches above are only example of the types of model fitting that may be conducted in the type of analysis disclosed by the inventors. Depending on the nature of the data set being modeled one of the above forms may be preferred, or perhaps a modification of the above models will be required. One skilled in the art will be able to develop alternative models by rearranging model terms or using different model forms, and, these modifications are within the scope of the present invention.

Figure 3:
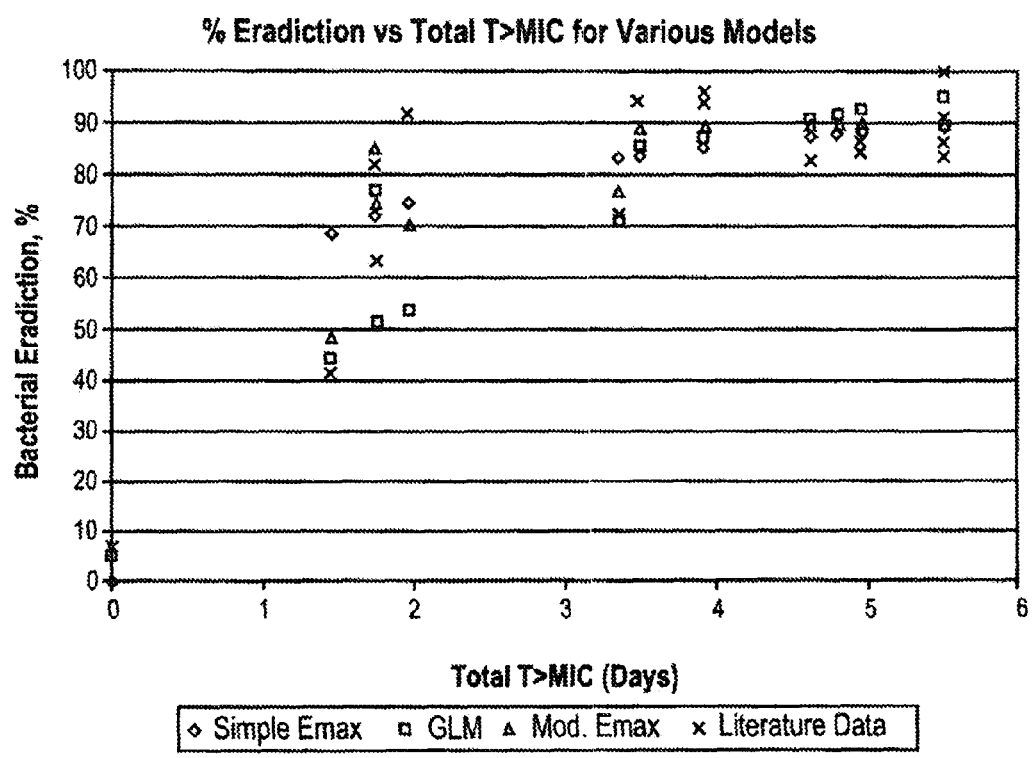
FIG. 3 is a plot showing the fitted data from the Simple Emax Model, General Linear Methodology Model (GLM), and Modified Multiple Parameter Emax Model (Mod. Emax) versus the actual literature data.

For further illustration, refer to FIG. 3, showing a plot of the fitted data from all models vs the actual literature data.

Figure 4:
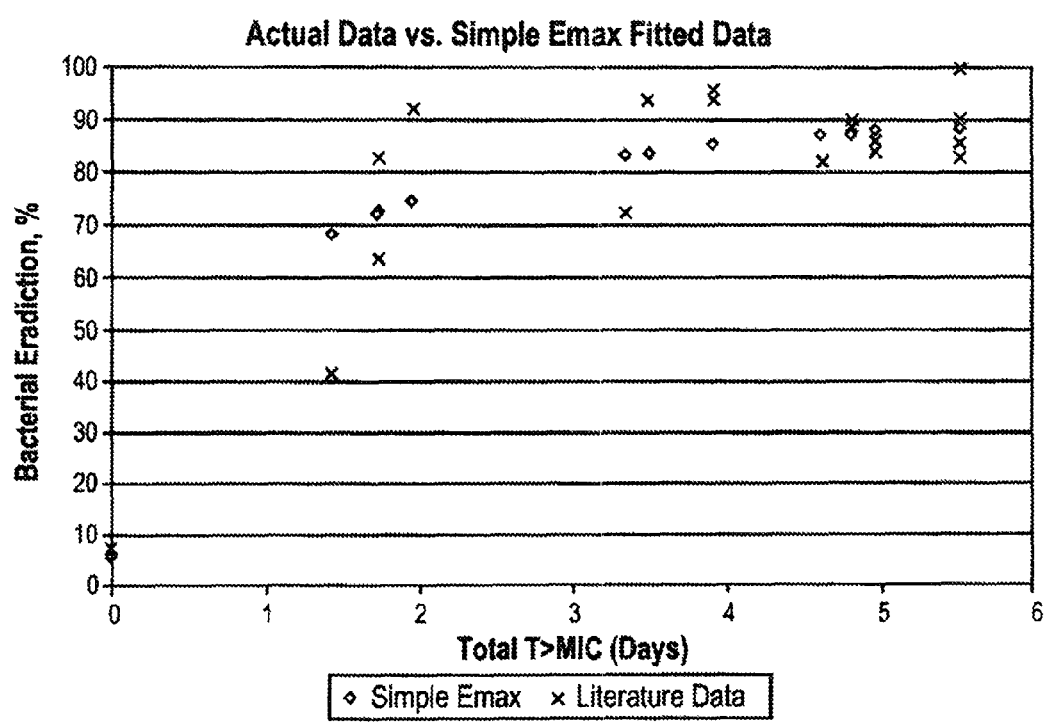
FIG. 4 is a plot showing the actual data versus the fitted data from the Simple Emax Model.

For further illustration, refer to FIG. 4, showing a plot of the actual data vs. the Simple Emax fitted Data.

Figure 5:
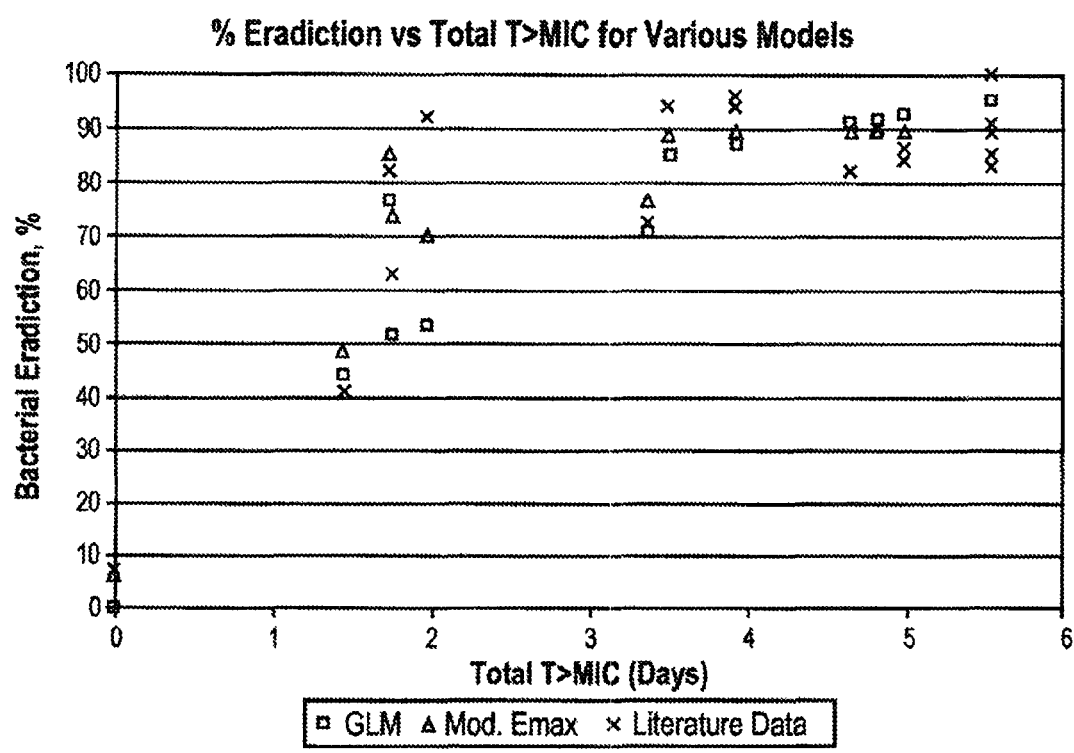
FIG. 5 is a plot showing the actual literature data versus the fitted data from the General Linear Methodology Model (GLM) and Modified Multiple Parameter Emax Model (Mod. Emax).

For further illustration, refer to FIG. 5, showing a plot of the actual literature data vs the GLM and modified Emax models.

In preferred embodiments of the product the desired percentage of eradication of the known bacterial pathogen is one that achieves clinical efficacy in the host for a condition caused by, or suspected to be caused by, the bacterial pathogen.

In a preferred embodiment of the product the antibiotic is a beta-lactam antibiotic. In a more preferred embodiment of the product the antibiotic is a penicillin antibiotic. In a particularly preferred embodiment of the product the antibiotic is amoxicillin.

In preferred embodiments of the method the desired percentage of eradication of the known bacterial pathogen is one that achieves clinical efficacy in the host for a condition caused by, or suspected to be caused by, the bacterial pathogen.

In a preferred embodiment of the method the antibiotic is a beta-lactam antibiotic. In a more preferred embodiment of the method the antibiotic is a penicillin antibiotic. In a particularly preferred embodiment of the method the antibiotic is amoxicillin.

In another embodiment of the invention, there is provided a once-a-day antibiotic product comprised of at least one modified release antibiotic dosage form. The modified release antibiotic dosage form comprises at least one antibiotic and a pharmaceutically acceptable carrier. The modified release antibiotic dosage form is formulated such that it contains the proper dose of antibiotic as a single unit for repeated once-daily administration in a treatment regimen of specified duration, whereby a plurality of once-daily administrations of the units ultimately achieves a desired "Total T>MIC" in the patient's blood.

In another embodiment of the invention, there is provided a method of therapeutically effectively treating a patient in need of treatment for bacterial infection, comprising administering a once-a-day antibiotic product comprised of at least one modified release antibiotic dosage form. The modified release antibiotic dosage form comprises at least one antibiotic and a pharmaceutically acceptable carrier. The modified release antibiotic dosage form is formulated such that it contains the proper dose of antibiotic as a single unit for repeated once-daily administration in a treatment regimen of specified duration, whereby a plurality of once-daily administrations of the units ultimately achieves a desired "Total T>MIC" in the patient's blood.

In another embodiment of the invention, there is provided a once-a-day antibiotic product comprised of at least one modified release antibiotic dosage form. The modified release antibiotic dosage form comprises at least one antibiotic and a pharmaceutically acceptable carrier. The modified release antibiotic dosage form is administered such that it provides the proper duration of antibiotic therapy as a single unit for repeated once-daily administration in a treatment regimen of specified daily dosage, whereby a plurality of once-daily administrations of the units ultimately achieves a desired "Total T>MIC" in the patient's blood.

In another embodiment of the invention, there is provided a method of therapeutically effectively treating a patient in need of treatment for bacterial infection, comprising administering a once-a-day antibiotic product comprised of at least one modified release antibiotic dosage form. The modified release antibiotic dosage form comprises at least one antibiotic and a pharmaceutically acceptable carrier. The modified release antibiotic dosage form is administered such that it provides the proper duration of antibiotic therapy as a single unit for repeated once-daily administration in a treatment regimen of specified daily dosage, whereby a plurality of once-daily administrations of the units ultimately achieves a desired "Total T>MIC" in the patient's blood.

Although embodiments of the instant invention allow for a Daily T>MIC that is less than that generally believed to be required in the art, in preferred embodiments the Daily T>MIC is generally not less than about 20%.

In one preferred embodiment the invention is directed to an antibiotic product that contains a beta-lactam antibiotic, as well as to the product's formulation and to its use in treating bacterial infections, wherein the infecting pathogen has an $MIC_{90} \geq 0.015$ μg/mL. for the beta-lactam antibiotic used. In a more preferred embodiment, the invention is directed to such an antibiotic product that contains a beta-lactam antibiotic, as well as to the product's formulation and to its use in treating bacterial infections, wherein the infecting pathogen has an $MIC_{90} \geq 0.015$ μg/mL. for the beta-lactam antibiotic used. In a particularly preferred embodiment, the invention is directed to such an antibiotic product that contains amoxicillin, as well as to the product's formulation and to its use in treating bacterial infections, wherein the infecting pathogen has an $MIC_{90} \geq 0.015$ μg/mL. for amoxicillin.

In accordance with an aspect of the invention there is provided a once-a-day beta-lactam antibiotic product for treating a bacterial infection in a patient or subject, comprising a beta-lactam antibiotic composition.

In particularly preferred embodiments the beta-lactam antibiotic is amoxicillin.

As herein-above discussed and herein-below discussed, the daily dosage of beta-lactam antibiotic will depend on various factors such as the bacterial pathogen to be targeted, the known resistance or susceptibility of the bacterial pathogen to the given beta-lactam antibiotic, and the known $MIC_{90}$ of the given bacterial pathogen for the given beta-lactam antibiotic.

Generally, the daily dosage of amoxicillin used in the invention comprises from about 250 to about 3000 mg. Preferably the daily dosage of amoxicillin used in the invention comprises from about 500 to about 2500 mg. More preferably the daily dosage of amoxicillin used in the invention comprises from about 775 to about 1550 mg.

In an embodiment the daily dosage of amoxicillin is 775 mg. and the optimal duration of therapy taking into account therapy, compliance, convenience, and marketing concerns, is 10 days.

In an embodiment the daily dosage of amoxicillin is 775 mg. and the optimal duration of therapy taking into account only efficacy concerns, is 10 days.

In a further aspect, the present invention provides a method of treating various indications in a patient, or in a subject, caused by bacterial pathogens, which treating comprises administering to the patient, or to the subject, once-a-day the herein-above described and herein-below described beta-lactam antibiotic compositions. As non-limiting examples of the indications for which the herein-above described and herein-below described beta-lactam antibiotic compositions may be used to treat a patient there may be mentioned: pharyngitis, tonsillitis, sinusitis, bronchitis, *pneumoniae*, ear infection (otitis media), uncomplicated skin and skin structure infections, and uncomplicated urinary infections.

As non-limiting examples of the infectious bacterial pathogens against which the herein-above described and herein-below described beta-lactam antibiotic compositions may be used there may be mentioned Aerobic Gram-positive microorganisms such as *Staphylococcus aureus, Streptococcus pneumoniae, Streptococcus pyogenes, Streptococcus agalactiae*, Streptococci (Groups C, F, G), and Viridans group streptococci; Aerobic Gram-negative microorganisms such as *Haemophilus influenzae, Haemophilus parainfluenzae, Moraxella catarrhalis, Bordetella pertussi, Legionalla pneumophila, Pasteurella multocida* and *Klebsiella pneumoniae*; Anaerobic Gram-positive microorganisms such as *Clostridium perfringens, Peptococcus niger*, and *Propionibacterium acnes*; Anaerobic Gram-negative microorganisms such as *Prevetolla melaminogenica* (formerly *Bacterocides melaminogenicus*); *Mycoplasma pneumoniae; Chlamydia pneumoniae; Mycobacterium avium* complex (MAC) consisting of *Mycobacterium avium* and/or *Mycobacterium intracellulare; Helicobacter pylori; Bacterocides fragilis; Fusobacterium nucleatum; Peptostreptococcus magnus; Peptostreptococcus micros*; and *Escherichia coli.*

In a preferred embodiment the composition is formulated to specifically target the bacterial pathogen *Streptococcus pyogenes.*

It will be appreciated by those of ordinary skill in the art that the methods and formulations hereinabove described and hereinbelow described for the beta-lactam antibiotic amoxicillin, or for other beta-lactam antibiotics, are also applicable to amoxicillin, or to other beta-lactam antibiotics, in combination with clavulanate, or in combination with other beta-lactamase inhibitors, particularly for treating infections where beta-lactamase producing pathogens are implicated.

While the hereinabove described and hereinbelow described compositions and methods may be used to improve the efficacy of any beta-lactam antibiotic, they are particularly useful for improving the efficacy of antibiotics that include a beta-lactam ring or a portion thereof, as non-limiting examples of such antibiotics there may be mentioned penicillin derivatives, such as penicillin V, penicillin G, penicillin, ampicillin, amoxicillin, carbenicillin, ticarcillin, piperacillin, nafcillin, cloxacillin, dicloxacillin, monobactams such as aztreonam, and carbapenems such as imipenem.

In accordance with another embodiment, the beta-lactam antibiotic composition has an overall release profile such that when administered the maximum serum concentration of the total antibiotic released from the composition is reached in less than twelve hours, preferably in less than eleven hours, and that maximum serum concentration is at least equivalent to the drug-specific $MIC_{90}$ of the bacterial pathogen.

In accordance with one embodiment of the invention, there are at least three dosage forms (at least one of which is a modified release dosage form). One of the at least three dosage forms is an immediate release dosage form whereby initiation of release of the beta-lactam antibiotic therefrom is not substantially delayed after administration of the beta-lactam antibiotic composition. The second and third of the at least three dosage forms are delayed release dosage forms (each of which may be a pH sensitive or a non-pH sensitive delayed dosage form, depending on the type of beta-lactam antibiotic composition), whereby the beta-lactam antibiotic released therefrom is delayed until after initiation of release of the beta-lactam antibiotic from the immediate release dosage form. More particularly, the beta-lactam antibiotic released from the second of the at least two dosage forms achieves a Cmax (maximum serum concentration in the serum) at a time after the beta-lactam antibiotic released from the first of the at least three dosage forms achieves a Cmax in the serum, and the beta-lactam antibiotic released from the third dosage form achieves a Cmax in the serum after the Cmax of beta-lactam antibiotic released from the second dosage form and the overall Cmax is at least equivalent to the drug-specific $MIC_{90}$ of the baterial pathogen.

In one embodiment, the second of the at least two dosage forms initiates release of the beta-lactam antibiotic contained therein at least one hour after the first dosage form, with the initiation of the release therefrom generally occurring no more than six hours after initiation of release of beta-lactam antibiotic from the first dosage form of the at least three dosage forms.

As hereinabove indicated, some embodiments of the beta-lactam antibiotic composition may contain three, four, or more different dosage forms (provided that at least one is a modified release dosage form).

In one three-dosage form embodiment, the beta-lactam antibiotic released from the third dosage form reaches a Cmax at a time later than the Cmax is achieved for the beta-lactam antibiotic released from each of the first and second dosage forms. In a preferred embodiment, release of beta-lactam antibiotic from the third dosage form is started after initiation of release of beta-lactam antibiotic from both the first dosage form and the second dosage form. In one embodiment, Cmax for beta-lactam antibiotic released from the third dosage form is achieved within eight hours.

In another three-dosage form embodiment the release of beta-lactam antibiotic from the second dosage form may be contemporaneous with initiation of release of beta-lactam antibiotic from the first dosage form.

In another three-dosage form embodiment the release of beta-lactam antibiotic from the third dosage form may be contemporaneous with initiation of release of beta-lactam antibiotic from the second dosage form.

In another embodiment, the beta-lactam antibiotic composition may contain four dosage forms (at least one of which is a modified release dosage form), with each of the four dosage forms having different release profiles, whereby the beta-lactam antibiotic released from each of the four different dosage forms achieves a Cmax at a different time.

As hereinabove indicated, in an embodiment, irrespective of whether the antibiotic contains at least two or at least three or at least four different dosage forms each with a different release profile, Cmax for all the beta-lactam antibiotic released from the beta-lactam antibiotic composition is achieved in less than twelve hours, and more generally is achieved in less than eleven hours and is at least equivalent to the drug-specific $MIC_{90}$ of the bacterial pathogen.

In a preferred embodiment, the beta-lactam antibiotic composition is a once a day composition, whereby after administration of the beta-lactam antibiotic composition, no further composition is administered during the day; i.e., the preferred regimen is that the composition is administered only once over a twenty-four hour period. Thus, in accordance with this preferred embodiment, there is a single administration of an beta-lactam antibiotic composition with the beta-lactam antibiotic being released in a manner such that overall beta-lactam antibiotic release is effected with different release profiles in a manner such that the overall Cmax for the beta-lactam antibiotic composition is reached in less than twelve hours and is at least equivalent to the drug-specific $MIC_{90}$ of the bacterial pathogen. The term single administration means that the total beta-lactam antibiotic administered over a twenty-four hour period is administered at the same time, which can be a single tablet or capsule or two or more thereof, provided that they are administered at essentially the same time.

In general, each of the dosage forms in the beta-lactam antibiotic compositions may have one or more beta-lactam antibiotics, and each of the dosage forms may have the same beta-lactam antibiotic or different beta-lactam antibiotics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic may occur. Such "leakage" is not "release" as used herein.

In one four-dosage form embodiment, the fourth dosage form may be a sustained release dosage form or a delayed release dosage form. If the fourth dosage form is a sustained release dosage form, even though Cmax of the fourth dosage form is reached after the Cmax of each of the other dosage forms is reached, beta-lactam antibiotic release from such fourth dosage form may be initiated prior to or after release from the second or third dosage form.

The beta-lactam antibiotic composition of the present invention, as hereinabove described, may be formulated for administration by a variety of routes of administration. For example, the beta-lactam antibiotic composition may be formulated in a way that is suitable for topical administration; administration in the eye or the ear; rectal or vaginal administration; as a nasal preparation; by inhalation; as an injectable; or for oral administration. In a preferred embodiment, the beta-lactam antibiotic composition is formulated in a manner such that it is suitable for oral administration.

For example, in formulating the beta-lactam antibiotic composition for topical administration, such as by application to the skin, the dosage forms, each of which contains a beta-lactam antibiotic, may be formulated for topical administration by including such dosage forms in an oil-in-water emulsion, or a water-in-oil emulsion. In such a formulation, an immediate release dosage form may be in the continuous phase, and a delayed release dosage form may be in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide a beta-lactam antibiotic composition in the form of a patch, which includes beta-lactam antibiotic dosage forms having different release profiles, as hereinabove described.

In addition, the beta-lactam antibiotic composition may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the beta-lactam antibiotic composition having at least one modified release dosage form (whether or not combined with additional dosage forms to provide a plurality of different release profiles) may be formulated for rectal or vaginal administration, as known in the art. This may take the form of a cream, an emulsion, a suppository, or other dissolvable dosage form similar to those used for topical administration.

In a preferred embodiment, the beta-lactam antibiotic composition is formulated in a manner suitable for oral administration. Thus, for example, for oral administration, each of the dosage forms may be used as a pellet or a particle, with a pellet or particle then being formed into a unitary pharmaceutical composition, for example, in a capsule, or embedded in a tablet, or suspended in a liquid for oral administration.

Alternatively, in formulating an oral delivery system, each of the dosage forms of the composition may be formulated as a tablet, with each of the tablets being put into a capsule to produce a unitary antibiotic composition. Thus, as a non-limiting example, a three dosage form antibiotic composition may include a first dosage form in the form of a tablet that is an immediate release tablet, and may also include two or more additional tablets, each of which provides for a delayed release or a sustained release of the beta-lactam antibiotic, as hereinabove described, to provide (and preferably maintain) a serum concentration of the beta-lactam antibiotic at least equivalent to the drug-specific $MIC_{90}$ of the bacterial pathogen.

The formulation of a beta-lactam antibiotic composition including at least three dosage forms with different release profiles for different routes of administration is deemed to be within the skill of the art from the teachings herein. As known in the art, with respect to delayed release, the time of release can be controlled by a variety of mechanisms such as pH, coating thickness, choice of polymer, and combinations of the foregoing.

In formulating a beta-lactam, antibiotic composition in accordance with one embodiment of the invention, an immediate release dosage form of the composition generally provides from about 20% to about 50% of the total dosage of beta-lactam antibiotic to be delivered by the composition, with such immediate release dosage form generally providing at least 25% of the total dosage of the beta-lactam antibiotic to be delivered by the composition. In many cases, an immediate release dosage form provides from about 20% to about 30% of the total dosage of beta-lactam antibiotic to be delivered by the composition; however, in some cases it may be desirable to have an immediate release dosage form provide for about 45% to about 50% of the total dosage of beta-lactam antibiotic to be delivered by the composition.

The remaining dosage forms deliver the remainder of the beta-lactam antibiotic. If more than one modified release dosage form is used each of the modified release dosage forms may provide about equal amounts of beta-lactam antibiotic; however, they may also be formulated so as to provide different amounts.

In accordance with the present invention, each of the dosage forms contains the same beta-lactam antibiotic; however, each of the dosage forms may contain more than one beta-lactam antibiotic.

In one embodiment, where the composition contains one immediate release component and two modified release components, the immediate release component provides from 20% to 35% (preferably 20% to 30%), by weight, of the total beta-lactam antibiotic; where there are three modified release components, the immediate release component provides from 15% to 30%, by weight, of the total beta-lactam antibiotic; and where there are four modified release components, the immediate release component provides from 10% to 25%, by weight, of the total beta-lactam antibiotic.

With respect to the modified release components, where there are two modified release components, the first modified release component (the one released earlier in time) provides from 30% to 60%, by weight, of the total beta-lactam antibiotic provided by the two modified release components with the second modified release component providing the remainder of the beta-lactam antibiotic.

Where there are three modified release components, the earliest released component provides 20% to 35% by weight of the total beta-lactam antibiotic provided by the three modified release components, the next in time modified release component provides from 20% to 40%, by weight, of the beta-lactam antibiotic provided by the three modified release components and the last in time providing the remainder of the beta-lactam antibiotic provided by the three modified release components.

When there are four modified release components, the earliest modified release component provides from 15% to 30%, by weight, the next in time modified release component provides from 15% to 30%, the next in time modified release component provides from 20% to 35%, by weight, and the last in time modified release component provides from 20% to 35%, by weight, in each case of the total beta-lactam antibiotic provided by the four modified release components.

The Immediate Release Component

The immediate release portion of this system can be a mixture of ingredients that breaks down quickly after administration to release the beta-lactam antibiotic. This can take the form of either a discrete pellet or granule that is mixed in with, or compressed with, the other three components.

The materials to be added to the beta-lactam antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the range of 0.05-15% (W/W).

The Non-pH Sensitive Delayed Release Component

The components in this composition are the same as the immediate release unit, but with additional polymers integrated into the composition, or as coatings over the pellet or granule.

Several methods to affect a delayed release with non-pH dependent polymers are known to those skilled in the art. These include soluble or erodible barrier systems, enzymatically degraded barrier systems, rupturable coating systems, and plugged capsule systems among others. These systems have been thoroughly described in the literature (see "A Review of Pulsatile Drug Delivery" by Bussemer and Bodmeier in the Winter 2001 issue of American Pharmaceutical Review) and formulations and methods for their manufacture are hereby incorporated by reference.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose; hydroxypropylmethylcellulose; hydroxypropylcellulose; hydroxyethylcellulose; carboxymethylcellulose; methylcellulose; nitrocellulose; Eudragit R; Eudragit RS; and Eudragit RL; Carbopol; or polyethylene glycols with molecular weights in excess of 8,000 daltons.

These materials can be present in concentrations from 4-20% (W/W).

When it is desired to delay inititiation of release of the sustained release dosage form, an appropriate coating may be used to delay inititiation of the sustained release, such as a pH sensitive or a non-pH sensitive coating.

The Non-pH Sensitive Coating for Sustained Release Dosage Form

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit RS), cellulose acetate, and ethylcellulose.

Typically these materials can be present in the range of 0.5-25% (W/W) of this component. Preferably the materials are present in an amount just enough to provide the desired in vivo lag time and $T_{max}$.

The pH Sensitive Coating for Sustained Release Dosage Form

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-20% (W/W) or more. Preferably the materials are present in an amount just enough to provide the desired in vivo lag time and $T_{max}$.

As hereinabove indicated, the units comprising the beta-lactam antibiotic composition of the present invention can be in the form of discrete pellets or particles contained in the capsule, or particles embedded in a tablet or suspended in a liquid suspension.

The beta-lactam antibiotic composition of the present invention may be administered, for example, by any of the following routes of administration: sublingual, transmucosal, transdermal, parenteral, etc., and preferably is administered orally. The composition includes a therapeutically effective amount of the beta-lactam antibiotic, which amount will vary with the beta-lactam antibiotic to be used, the disease or infection to be treated, and the number of times that the composition is to be delivered in a day. The composition is administered to a patient or subject in an amount effective for treating a bacterial infection.

This system will be especially useful in extending the practical therapeutic activity for antibiotics with elimination half lives of less than 20 hours and more particularly with elimination half-lives of less than 12 hours, and will be particularly useful for those drugs with half-lives of 2-10 hours.

The following are examples of some antibiotics with half-lives of about 1 to 12 hours: imipenem, ertapenem, (carbapenems) penicillin V, penicillin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, (penicillins).

The beta-lactam antibiotic composition should be administered for a sufficient amount of time to treat the infection. In one embodiment the beta-lactam antibiotic composition is administered for 10 days.

The invention will be further described with respect to the following examples; however, the scope of the invention is not limited thereby. All percentages in this specification, unless otherwise specified, are by weight.

The following examples detail the general procedures for making immediate release, delayed release (both pH sensitive and non-pH sensitive types), sustained release, and delayed sustained release components for the dosage form of the present invention. Any combination of the components that results in the desired time above MIC would be included as part of this disclosure. Specific examples of combinations of the components are given, but are not limited to the ones described herein. Additionally, there is an example of a multi-unit dosage form specific to amoxicillin type tablets, but any appropriate therapeutic agent could be substituted.

EXAMPLES

I. Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum oven or forced-air oven. The product may be sieved or granulated, and compressed using a suitable tablet press, such as a rotary tablet press, or filled into a capsule or sachet with a suitable filler.

|  | Ingredient | Conc. (% W/W) |
| --- | --- | --- |
| Example 1: | Amoxicillin | 65% (W/W) |
|  | Microcrystalline cellulose | 20 |
|  | Povidone | 10 |
|  | Croscarmellose sodium | 5 |
| Example 2: | Amoxicillin | 55% (W/W) |
|  | Microcrystalline cellulose | 25 |
|  | Povidone | 10 |
|  | Croscarmellose sodium | 10 |
| Example 3: | Amoxicillin | 65% (W/W) |
|  | Microcrystalline cellulose | 20 |
|  | Hydroxypropylcellulose | 10 |
|  | Croscarmellose sodium | 5 |
| Example 4: | Amoxicillin | 75% (W/W) |
|  | Polyethylene glycol 4000 | 10 |
|  | Polyethylene glycol 2000 | 10 |
|  | Hydroxypropylcellulose | 5 |
| Example 5: | Amoxicillin | 75% (W/W) |
|  | Polyethylene glycol 8000 | 20 |
|  | Polyvinylpyrrolidone | 5 |
| Example 6: | Clarithromycin | 65% (W/W) |
|  | Microcrystalline cellulose | 20 |
|  | Hydroxypropylcellulose | 10 |
|  | Croscarmellose sodium | 5 |

| | Ingredient | Conc. (% W/W) |
|---|---|---|
| Example 7: | Clarithromycin | 75% (W/W) |
| | Microcrystalline cellulose | 15 |
| | Hydroxypropylcellulose | 5 |
| | Croscarmellose sodium | 5 |
| Example 8: | Clarithromycin | 75% (W/W) |
| | Polyethylene glycol 4000 | 10 |
| | Polyethylene glycol 2000 | 10 |
| | Hydroxypropylcellulose | 5 |
| Example 9: | Clarithromycin | 75% (W/W) |
| | Polyethylene glycol 8000 | 20 |
| | Polyvinylpyrrolidone | 5 |
| Example 10: | Ciprofloxacin | 65% (W/W) |
| | Microcrystalline cellulose | 20 |
| | Hydroxypropylcellulose | 10 |
| | Croscarmellose sodium | 5 |
| Example 11: | Ciprofloxacin | 75% (W/W) |
| | Microcrystalline cellulose | 15 |
| | Hydroxypropylcellulose | 5 |
| | Croscarmellose sodium | 5 |
| Example 12: | Ciprofloxacin | 75% (W/W) |
| | Polyethylene glycol 4000 | 10 |
| | Polytheylene glycol 2000 | 10 |
| | Hydroxypropylcellulose | 5 |
| Example 13: | Ciprofloxacin | 75% (W/W) |
| | Polyethylene glycol 8000 | 20 |
| | Polyvinylpyrrolidone | 5 |
| Example 14: | Ceftibuten | 75% (W/W) |
| | Polyethylene glycol 4000 | 10 |
| | Polyethylene glycol 2000 | 10 |
| | Hydroxypropylcellulose | 5 |
| Example 15: | Ceftibuten | 75% (W/W) |
| | Polyethylene Glycol 4000 | 20 |
| | Polyvinylpyrrolidone | 5 |

II. Non-pH Sensitive Delayed Release Component

Any of the methods described in "A Review of Pulsatile Drug Delivery" by Bussemer and Bodmeier in the Winter 2001 issue of American Pharmaceutical Review may be utilized to make the pH independent delayed release component described. Examples 16 and 17 utilize an organic acid layer underneath a layer of Eudragit RS to result in a rapid increase in the permeability of the Eudragit film after a set amount of time depending on the permeability and thickness of the film thus allowing the inner core to release through the Eudragit membrane. Example 18 utilizes a core with a highly swellable polymer that ruptures the insoluble coating membrane after a certain amount of time determined by the permeability, plasticity and thickness of the external cellulose acetate membrane. The coatings are applied to the core via methods such as wurster column coating in a fluid bed processor as known to those skilled in the art.

Additionally, this component may be formed as in example 19. In this example the component is prepared by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven.

After the component is allowed to cool, the product may be sieved or granulated, and compressed using a suitable tablet press, such as a rotary tablet press, or filled into a capsule with a suitable encapsulator.

| | Ingredient | Conc. (% W/W) |
|---|---|---|
| Example 16: | Core from Example 4 | 65% (W/W) |
| | Citric Acid | 10 |
| | Eudragit RS Polymer | 20 |
| | Talc | 4 |
| | TEC | 1 |
| Example 17: | Core from Example 9 | 75% (W/W) |
| | Citric Acid | 10 |
| | Eudragit RS Polymer | 10 |
| | Talc | 4 |
| | TEC | 1 |
| Example 18: | Core from Example 1 | 93% (W/W) |
| | Cellulose Acetate | 6.75 |
| | PEG 400 | 0.25 |
| Example 19: | Ciprofloxacin | 70% (W/W) |
| | Polyox | 20 |
| | Hydroxypropylcellulose | 5 |
| | Croscarmellose sodium | 5 |

III. Enteric Release Component

Examples 20-27 utilize film coating techniques commonly known to those skilled in the art to create the enteric release component by layering of such enteric polymers onto an active core. In general the steps involve first making a coating dispersion or solution in organic or aqueous solvent. Second, the coating is applied at the proper conditions to produce an acceptably uniform film. This is done in a suitable coating apparatus such as a pan coater or a fluid bed wurster column coater. Optionally the product may be further cured if necessary.

To create a matrix type enteric component, formulate the ingredients of examples 28-32 by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool.

The product produced by either manner may be sieved or granulated, and compressed using a suitable tablet press, such as a rotary tablet press, or filled into capsules using a suitable capsule filler such as a MG2 Futura.

| | Ingredient | Conc. (% W/W) |
|---|---|---|
| Example 20: | Core from Example 1 | 65% (W/W) |
| | Cellulose Acetate Pthalate | 30 |
| | TEC | 5 |
| Example 21: | Core from Example 5 | 75% (W/W) |
| | Cellulose Acetate Pthalate | 20 |
| | Triacetin | 5 |
| Example 22: | Core from Example 1 | 65% (W/W) |
| | Eudragil L | 25 |
| | Talc | 8 |
| | TEC | 2 |
| Example 23: | Core from Example 1 | 65% (W/W) |
| | Eudragit FS | 28 |
| | Talc | 5 |
| | TEC | 2 |
| Example 24: | Core from Example 1 | 65% (W/W) |
| | Eudragit S | 28 |
| | Talc | 5 |
| | TEC | 2 |
| Example 25: | Core from Example 7 | 75% (W/W) |
| | Eudragit L | 20 |
| | Talc | 3.5 |
| | TEC | 1.5 |

-continued

| | Ingredient | Conc. (% W/W) |
|---|---|---|
| Example 26: | Core from Example 11 | 60% (W/W) |
| | Eudragit L | 35 |
| | Talc | 4 |
| | TEC | 1 |
| Example 27: | Core from Example 15 | 65% (W/W) |
| | Cellulose Acetate Pthalate | 32.5 |
| | TEC | 2.5 |
| Example 28: | Amoxicillin | 75% (W/W) |
| | Microcrystalline Cellulose | 5 |
| | Hydroxypropylcellulose pthalate | 20 |
| Example 29: | Amoxicillin | 60% (W/W) |
| | Lactose | 10 |
| | Eudragit L 30D | 30 |
| Example 30: | Ciprofloxacin | 70% (W/W) |
| | Polyethylene glycol 4000 | 10 |
| | Cellulose acetate pthalate | 20 |
| Example 31: | Clarithromycin | 60% (W/W) |
| | Polyethylene glycol 2000 | 10 |
| | Lactose | 20 |
| | Eudragit L 30D | 10 |
| Example 32: | Ceftibuten | 70% (W/W) |
| | Microcrystalline cellulose | 20 |
| | Cellulose acetate pthalate | 10 |

IV. Sustained Release Component

Examples 33-38 utilize film coating techniques commonly known to those skilled in the art to create the sustained release component by layering of such sustained release polymers onto an active core. In general the steps involve first making a coating dispersion or solution in organic or aqueous solvent. Second, the coating is applied at the proper conditions to produce an acceptably uniform film. This is done in a suitable coating apparatus such as a pan coater or a fluid bed wurster column coater. Optionally the product may be further cured if necessary. Curing studies are recommended with sustained release membranes.

To create a matrix type sustained release component, formulate the ingredients of example 39-42 by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool.

The product produced by either manner may be sieved or granulated, and compressed using a suitable tablet press, such as a rotary tablet press, or filled into capsules using a suitable capsule filler such as a MG2 Futura.

| | Ingredient | Conc. (% W/W) |
|---|---|---|
| Example 33: | Core from Example 1 | 75% (W/W) |
| | Ethylcellulose | 20 |
| | HPC | 5 |
| Example 34: | Core from Example 5 | 80% (W/W) |
| | Eudragit RS | 10 |
| | Eudragit RL | 5 |
| | Talc | 3 |
| | TEC | 2 |
| Example 35: | Core from Example 5 | 90% (W/W) |
| | Ethylcellulose | 9 |
| | Triacetin | 1 |
| Example 36: | Core from Example 7 | 90% (W/W) |
| | Surelease | 10 |
| Example 37: | Core from Example 11 | 85% (W/W) |
| | Kollicoat SR | 10 |
| | TBC | 5 |

| | Ingredient | Conc. (% W/W) |
|---|---|---|
| Example 38: | Core from Example 15 | 80% (W/W) |
| | Polyethylene glycol 8000 | 5 |
| | Eudgragit RS 30D | 15 |
| Example 39: | Amoxicillin | 75% (W/W) |
| | Hydroxyethylcellulose | 10 |
| | Polyethylene glycol 4000 | 10 |
| | Hydroxypropylcellulose | 5 |
| Example 40: | Ciprofloxacin | 75% (W/W) |
| | Lactose | 10 |
| | Povidone (PVP) | 10 |
| | Polyethylene glycol 2000 | 5 |
| Example 41: | Clarithromycin | 75% (W/W) |
| | Polyethylene glycol 4000 | 10 |
| | Povidone (PVP) | 10 |
| | Hydroxypropylcellulose | 5 |
| Example 42: | Ceftibuten | 75% (W/W) |
| | Lactose | 15 |
| | Polyethylene glycol 4000 | 5 |
| | Polyvinylpyrrolidone | 5 |

III. Sustained Release Dosage Form with Coating to Delay Initiation of Sustained Release Delaying the initiation of the sustained release of antibiotic in the present invention is achieved by either coating the immediate release component bead with a sustained release coating and then subsequently applying an enteric coating or non pH sensitive delayed release coating to that coated bead, or alternatively the sustained release matrix component bead may be coated with an enteric coating or non pH sensitive delayed release coating.

Coatings can be applied to either the sustained release coated beads or the sustained release matrix beads to form a product which pulses the therapeutical agent in a desired environment or location of the GI tract.

III A. The following examples describe the detailed preparation of the sustained-release coating materials to be applied to the immediate release beads from section I of the examples, resulting in a sustained release component of the invention.

Example 43

Eudragit RS Example—Organic Coating

| Component Part A | Percentage (%) |
|---|---|
| Eudragit RS-100 | 6.0 |
| Triethyl Citrate | 1.0 |
| Talc | 0.5 |
| Acetone | 92.5 |

Step 1. Dissolve Eudragit in Acetone.

Step 2. Mix TEC and talc in a separate container with some Acetone.

Step 3. Add step 2 to Step 1, and allow to mix for 20 minutes before spraying.

Example 44

Surelease™ Example—Aqueous Coating

| Component Part A | Percentage (%) |
|---|---|
| Surelease | 90 |
| Purified Water | 10.0 |

Step 1. Mix surelease and water for 30 minutes before spraying.

Directions for application of the sustained release coating to the beads:

Charge a wurster column equipped fluid bed with the beads to be coated. Spray the coating onto the beads at a rate and temperature known to those skilled in the art of bead coating so as to efficiently coat the beads to give a weight gain of between 4 and 20%. Dry the beads to the specified level of coating solvent for optimum handling and stability. Cure the beads for additional congealing of the sustained release film if required.

III B. The following are examples of the pH sensitive, or enteric release, coating that can be used to optionally delay the onset of action of any or all of the second, third, or additional dosage forms.

The composition of the aqueous Eudragit L30D-55 dispersion to be applied to the immediate release components that have been treated with the above-described sustained release coatings, or to the sustained-matrix pellets is provided below in Example 45.

Example 45

Eudragit® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

Preparation Procedure for an Eudragit® L 30 D-55 Aqueous Dispersion

Step 1 Suspend triethyl citrate and talc in deionized water.
Step 2 The TEC/talc suspension is then homogenized using a PowerGen 700 high shear mixer.
Step 3 Add the TEC/talc suspension slowly to the Eudragit® L 30 D-55 latex dispersion while stirring.
Step 4 Allow the coating dispersion to stir for one hour prior to application onto the matrix pellets.

Example 46

Preparation of an Eudragit® S 100 Aqueous Coating Dispersion

Dispersion Formulation

The composition of the aqueous Eudragit® S 100 dispersion applied to the matrix pellets is provided below:

Eudragit® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

Preparation Procedure for an Eudragit® S 100 Aqueous Dispersion

Part I:
 (i) Dispense Eudragit® S 100 powder in deionized water with stirring.
 (ii) Add ammonium hydroxide solution drop-wise into the dispersion with stirring.
 (iii) Allow the partially neutralized dispersion to stir for 60 minutes.
 (iv) Add triethyl citrate drop-wise into the dispersion with stirring. Stir for about 2 hours prior to the addition of Part B.

Part II:
 (i) Disperse talc in the required amount of water
 (ii) Homogenize the dispersion using a PowerGen 700D high shear mixer.
 (iii) Part B is then added slowly to the polymer dispersion in Part A with a mild stirring.

Coating Conditions for the Application of Aqueous Coating Dispersions

The following coating parameters were used to coat matrix pellets with each of the Eudragit® L 30 D-55 and Eudragit® S 100 aqueous film coating.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
 (ii) Coat matrix pellets with S100 dispersion such that you apply 20% coat weight gain to the pellets.

III. C. The following examples describe the detailed preparation of the non pH sensitive coating materials to be used to optionally delay the onset of action of any or all of the second, third, or additional dosage forms.

Example 47

Rupturable Film

| Component Part A | Percentage (%) |
|---|---|
| Cellulose Acetate 398-10 | 6.0 |
| PEG 400 | 1.5 |
| Acetone | 92.5 |

Step 1. Dissolve cellulose acetate in Acetone.
Step 2. Add TEC to Step 1, and allow to mix for 20 minutes.
Directions for application of the sustained release coating to the beads:

Charge a wurster column equipped fluid bed with the beads to be coated. The beads must contain a component which will swell rapidly upon exposure to moisture. Beads containing croscarmellose sodium in Section I are good candidates as are beads with swellable hydrophilic polymers from Section II. Spray the coating onto the beads at a rate and temperature known to those skilled in the art of bead coating so as to efficiently coat the beads to give a weight gain of between 4 and 20%. Dry the beads to the specified level of coating solvent for optimum handling and stability.

Coating Conditions for the application of the rupturable film coating.

The following coating parameters were used to coat matrix mini tablets from a previous example with the rupturable film coating. A 2.5% weight gain provided the desired lag time.

| | |
|---|---|
| Coating Equipment | Vector LDCS Coating System with 1.3 L pan |
| Spray nozzle diameter | 0.8 mm |
| Material Charge | 800 grams |
| Inlet Air Temperature | 40 to 45° C. |
| Outlet Air Temperature | 18 to 23° C. |
| Atomization Air Pressure | 25 psi |
| Pump Rate | 6 grams per minute |

The enteric coatings and non-pH sensitive coatings as described above can be applied to either a sustained release matrix bead as in examples 16-25, or to the immediate release component beads that have been previously treated with a sustained release coating, to thereby provide a sustained release bead with a delayed onset of action. In addition, the enteric coating or non-pH sensitive coating can be applied to the immediate release component bead directly to provide delayed onset of action.

IV. Example Final Compositions

After one or all of the desired individual components are manufactured, the final dosage form is assembled and may take the shape of a tablet, capsule or sachet. Preferably the final dosage form takes the shape of a capsule or tablet. Most preferably the final dosage form is a tablet.

One or more of the individual components can be used to achieve the desired Daily T>MIC. If one were to include three components in one's dosage form then preferably the first, second, and third dosage forms provide 20-70%, 10-70% and 10-70% of the total dosage form, respectively. More preferably the ratio of first, second and third dosage forms are in the range of 25-66%, 15-60% and 15-60% of the total dosage form respectively. Most preferably the ratio of the first, second and third dosage forms are in the range of 33-60%, 25-50%, and 25-50% respectively. One can also utilize one, two, three, or four or more components, and balance the ratio of the components in such a way to meet the Daily T>MIC criteria.

V. Example of Three Component Amoxicillin Tablet and Sprinkle Dosage Forms

V-1. Description of the Dosage Form

API content can range for example from 10 to 80% therapeutic compound, and in the case the therapeutic compound is amoxicillin, it most preferably would contain 775 mg amoxicillin. The tablet can be of any desired shape, with a target gross weight of approximately 1500 mg. The tablet can optionally be coated with a film, and/or imprinted.

The following specific example is written for components that contain amoxicillin, however other therapeutic agents can be substituted with proper proportion adjustments known to one skilled in the art of oral dosage form development.

The tablet of this invention is a rapidly disintegrating formulation containing three active intermediate compositions, an immediate-release granulation (Amoxicillin Granules) and two functionally coated delayed-release pellets (Amoxicillin Pulse 2 Pellets and Amoxicillin Pulse 3 Pellets). Non-functional, color and clear film coats are optionally applied to the outer surface and/or the coated tablets are imprinted.

FIG. 1 is a flowchart describing the General Procedure to Make a Multiparticulate Tablet.

Table 1 provides the qualitative and quantitative composition of three example amoxicillin tablet formulations on a weight to weight (w/w %) basis of individual ingredients. For formulation B, an example set of procedures and component compositions for making this type of tablet is expanded. Table 2 provides the qualitative and quantitative composition of an example amoxicillin Tablet formulation on the basis of the tablet core, coatings, and its active intermediate compositions. Tables 3, 4, 5, and 6 provide the qualitative and quantitative composition of the Amoxicillin Granules, Amoxicillin Core Pellets, Amoxicillin Pulse 2 Pellets, and Amoxicillin Pulse 3 Pellets, respectively. An optional coating can be applied and optional tablet imprinting can be used to complete the product presentation.

TABLE 1

Example Quantitative Compositions of Example Amoxicillin Tablets.

| Component | A (w/w %) | B (w/w %) | C (w/w %) |
|---|---|---|---|
| Amoxicillin, USP | 78.476 | 59.524 | 62.821 |
| Silicified Microcrystalline Cellulose | 0.000 | 20.676 | 21.900 |
| Crospovidone, NF | 0.000 | 3.892 | 4.100 |
| Methacrylic Acid Copolymer Dispersion, NF | 4.272 | 2.926 | 2.879 |
| Opadry ® Blue[1] | 0.000 | 2.415 | 0.000 |
| Talc, USP | 3.617 | 2.036 | 1.804 |
| Hydroxypropyl Methylcellulose Acetate Succinate[1] | 4.107 | 1.939 | 1.229 |

TABLE 1-continued

Example Quantitative Compositions of Example Amoxicillin Tablets.

| Component | A (w/w %) | B (w/w %) | C (w/w %) |
|---|---|---|---|
| Microcrystalline Cellulose, NF | 4.276 | 1.787 | 1.545 |
| Povidone, USP | 1.716 | 1.546 | 1.691 |
| Opadry ® Clear[1] | 0.000 | 0.966 | 0.000 |
| Magnesium Stearate, NF | 0.000 | 0.966 | 1.000 |
| Triethyl Citrate, NF | 1.806 | 0.939 | 0.694 |
| Polyoxyl 35 Castor Oil, NF | 0.843 | 0.345 | 0.299 |
| Sodium Lauryl Sulfate, NF | 0.129 | 0.0152 | 0.039 |
| Opadry II White, 33G28523 | 0.761 | 0.000 | 0.000 |
| Opacode ® Black[1] | 0.000 | Trace Amount | 0.0 |
| Purified Water, USP[1] | * | * | * |
| Total | 100.0 | 100.0 | 100.0 |

[1]Water removed during processing

TABLE 2

Composition of an Example Amoxicillin Tablet by component.

| Core Tablet | w/w % |
|---|---|
| Amoxicillin Granules | 28.6 |
| Amoxicillin Pulse 2 Pellets | 24.1 |
| Amoxicillin Pulse 3 Pellets | 20.9 |
| Silicified Microcrystalline Cellulose | 21.4 |
| Crospovidone | 4.0 |
| Magnesium Stearate | 1.0 |
| Core Tablet Weight | 100 |

V-2 Amoxicillin Granules

TABLE 3

Qualitative and Quantitative Composition of Amoxicillin Granules

| Component | w/w % |
|---|---|
| Amoxicillin | 97.0 |
| Povidone | 3.0 |
| Purified Water[1] | N/A |
| Total Amoxicillin Granules | 100 |

[1]Water removed during processing

General Procedure for Manufacturing Amoxicillin Granules:

A standard wet granulation process known to one skilled in the art is used for preparation of the Amoxicillin Granules. The wet granules are discharged and fed into a Dome Extrusion Granulator. The wet extruded granules are then dried for a fixed period of time or until the LOD (loss on drying) of the granules is suitable for the formulation, typically less than 15%. The dried granules are then sized in a Rotating Impeller Screening Mill. The milled material is collected into drums.

V-3 Amoxicillin Core Pellets

The Core Pellets are used as the starting material for the later preparation of the Pulse 2 Pellets and the Pulse 3 Pellets used in the tablet preparation. They also serve as the core pellet for the immediate release pellet in the sprinkle dosage form. The core pellets are prepared using the unit operations of wet granulating, extruding, spheronizing, fluid bed drying and sizing. The composition of the core pellets is listed in Table 4.

TABLE 4

Composition of Amoxicillin Core Pellets

| Amoxicillin Trihydrate (92%) Pellet Component | w/w % |
|---|---|
| Amoxicillin Trihydrate, Powder Grade, USP | 92.0 |
| Microcrystalline Cellulose, NF | 5.0 |
| Povidone K30, USP | 2.0 |
| Polyoxyl 35 Castor Oil, NF | 1.0 |
| Total | 100 |

V-4 Amoxicillin Pulse 2 Pellets

Table 5 lists the composition of the example Amoxicillin Pulse 2 Pellets.

TABLE 5

Composition of Amoxicillin Pulse 2 Pellets

| Component | w/w % |
|---|---|
| Amoxicillin | 76.6 |
| Microcrystalline Cellulose (Avicel ® PH-101) | 4.19 |
| Povidone (Kollidon 30) | 1.69 |
| Polyoxyl 35 Castor Oil (Cremophor EL) | 0.80 |
| Methacrylic Acid Copolymer Dispersion (Eudragit ® L30D-55)[1] | 10.41 |
| Talc | 5.19 |
| Triethyl Citrate | 1.00 |
| Purified Water[2] | N/A |
| Total Amoxicillin Pulse 2 Pellets | 100.0 |

[1]Amount per tablet of the solids content
[2]Water removed during processing

The Amoxicillin Pulse 2 Pellets are prepared by coating the previously prepared Amoxicillin Core Pellets with a functional film coat of methacrylic acid copolymer dispersion, 20% W/w. Prior to the coating process, a dispersion of the methacrylic acid copolymer is made according to the manufacturer's instructions. The dispersion is applied to the Amoxicillin Core pellets using a Fluid Bed Bottom Spray Coater, equipped with appropriate spray nozzles and a fixed column gap distance.

The pellets are then appropriately sized. The Amoxicillin Pulse 2 Pellets may be held in ambient warehouse conditions until further processing.

V-5 Amoxicillin Pulse 3 Pellets

The amoxicillin pulse 3 pellets are prepared by coating the previously prepared Amoxicillin Core Pellets with a 5% w/w subcoat of methacrylic acid copolymer, followed by a 20% w/w functional film coat of hypromellose acetate succinate.

Table 6 lists the composition of the example amoxicillin Pulse 3 pellets

TABLE 6

Composition of Amoxicillin Pulse 3 Pellets

| Component | Amount/Tablet (mg) |
| --- | --- |
| Amoxicillin | 222.6 |
| Microcrystalline Cellulose (Avicel ® PH-101) | 12.1 |
| Povidone (Kollidon 30) | 4.8 |
| Polyoxyl 35 Castor Oil (Cremophor EL) | 2.4 |
| Methacrylic Acid Copolymer Dispersion (Eudragit ® L30D-55)[1] | 7.6 |
| Hypromellose Acetate Succinate (AQOAT AS-HF) | 29.0 |
| Talc | 12.4 |
| Triethyl Citrate | 10.6 |
| Sodium Lauryl Sulfate | 0.9 |
| Purified Water[2] | N/A |
| Total Amoxicillin Pulse 3 Pellets | 302.4 |

[1]Amount per tablet of the solids content
[2]Water removed during processing

Prior to the subcoating process, a dispersion of the methacrylic acid copolymer is made according to the manufacturer's instructions. The second coating material, the hypromellose acetate succinate dispersion is prepared according to the manufacturer's instructions. The subcoat layer, is then applied to the Amoxicillin Core Pellets using the same Fluid Bed Bottom Spray Coater as used for preparation of the Pulse 2 Pellets.

The hypromellose acetate succinate coating dispersion is then immediately applied to the sub-coated pellets still in the Fluid Bed Bottom Spray Coater. The atomization air used for the second coating process is set at the same pressure as used for the sub coating process. The coating process is complete when all of the dispersion has been applied. Following a drying period the final coated pellets are cooled.

The coated, dried and cooled Amoxicillin Pulse 3 Pellets are collected into lined drums The coated Pulse 3 Pellets are then sized. The Amoxicillin Pulse 3 Pellets may be held in ambient warehouse conditions until further processing.

V-6 Tabletting

The amoxicillin granules, pulse 2 pellets and pulse 3 pellets can be combined at the desired ratio and compressed on a rotary or other type of tablet press with suitable tooling installed for the desired size tablet. Ratios of Pulses or pellets can vary depending on the absorption characteristics of the desired drug. Ratios can range from front loaded (middle loaded or back loaded as per discussion in the specs section. The percent of each component can range from 10-90% for each of the at least 3 components in this example. For example, but not in anyway limiting, pulse 1 can be 10%, pulse 2 can be 80% and pulse 3 can be 10%. Or, as an alternate non-limiting example, pulse 1 can be 30%, pulse 2 can be 50% and pulse 3 can be 20%. In a preferred embodiment the tablet is manufactured by combining the immediate-release granulation (Pulse 1, 45%) with two functionally coated delayed-release pellets (Pulse 2, 30% and Pulse 3, 25%).

V-7 Optional Coatings

An additional optional coating can be applied to the tablet, or directly to the core, pulse 2 and pulse 3 pellets according to the manufacturer's recommendation for the coating process conditions and procedures.

An optional printing on the tablets can be done using a formula as supplied by the manufacturer or as modified to suit the tablet characteristics. Additional optional ingredients are Microcrystalline Cellulose and Colloidal Silicon Dioxide. These can be added to prevent tacking and sticking if necessary. These two materials can be optionally obtained as the composition Prosolv SMCC® 90 (FMC).

V-8 Sprinkle Dosage Form

These coated or uncoated pellets can be filled to give the desired dose into an appropriate dosing device at the desired ratios as described above either separately or all together, such as a sachet, capsule, or other means of delivering the material to the consumer. Numerous modification and variations of the present invention are possible in light of the above teachings and therefore within the scope of the appended claims the invention may be practiced otherwise than as particularly described. The present invention also extends to formulations which are bioequivalent to the pharmaceutical formulations of the present invention, in terms of both rate and extent of absorption, for instance as defined by the US Food and Drug Administration and discussed in the so-called "Orange Book" (Approved Drug Compositions with Therapeutic Equivalence Evaluations, US Dept of Health and Human Services, 19th edn, 1999).

We claim:

1. A process for treating a patient for at least one of pharyngitis or tonsillitis, caused by, or suspected to be caused by, an infection of said patient by Streptococcus pyogenes, said process for treating comprising: orally administering to said patient 775 mg of amoxicillin once a day, for ten days; wherein said amoxicillin is administered in a pharmaceutical product comprising an immediate release dosage form, a first delayed release dosage form and a second delayed release dosage form, wherein said first delayed release dosage form initiates release of amoxicillin after said immediate release dosage form initiates release of amoxicillin, and wherein said second delayed release dosage form initiates release of amoxicillin after said first delayed release dosage form initiates release of amoxicillin, whereby a Total T>MIC sufficient to achieve at least an 85% bacterial eradication rate is achieved in the patient.

2. The process of claim 1, wherein said pharmaceutical product is in tablet form.

3. The process of claim 1, wherein said pharmaceutical product is in the form of a plurality of tablets.

4. The process of claim 1, wherein said pharmaceutical product is in tablet form wherein, said immediate release dosage form comprises 45% of the tablet, wherein said first delayed release dosage form comprises 30% of the tablet, and wherein said second delayed release dosage form comprises 25% of the tablet.

5. The process of claim 1, wherein said pharmaceutical product is in capsule form.

6. The process of claim 1, wherein said pharmaceutical product is in the form of a plurality of capsules.

7. The process of claim 1, wherein said pharmaceutical product is in the form of pellets or particles suspended in a liquid.

8. The process of claim 1, wherein said pharmaceutical product is in the form of a sachet.

9. The process of claim 1, wherein said pharmaceutical product is in the form of a sprinkle.

10. The process of claim 1, wherein the Total T>MIC sufficient to achieve at least a 90% bacterial eradication rate is achieved in the patient.

* * * * *